US007043372B2

(12) United States Patent
Koehler et al.

(10) Patent No.: US 7,043,372 B2
(45) Date of Patent: May 9, 2006

(54) FLUID CONDITION MONITORING USING BROAD SPECTRUM IMPEDANCE SPECTROSCOPY

(75) Inventors: Charles J. Koehler, Milwaukee, WI (US); David L. Wooton, Beaverdam, VA (US); David R. Sosnowski, Lake Orion, MI (US); Richard W. Hirthe, Milwaukee, WI (US)

(73) Assignee: Eaton Corporation, Cleveland, OH (US)

( * ) Notice: Subject to any disclaimer, the term of this patent is extended or adjusted under 35 U.S.C. 154(b) by 96 days.

(21) Appl. No.: 10/723,624

(22) Filed: Nov. 26, 2003

(65) Prior Publication Data
US 2005/0110503 A1 May 26, 2005

(51) Int. Cl.
*G01N 31/00* (2006.01)
(52) U.S. Cl. .......................... 702/25; 702/30; 324/693
(58) Field of Classification Search ............ 702/22–25, 702/27, 28, 30–32, 50, 52, 53, 55, 57, 64, 702/65, 66, 179, 183, 184; 324/434, 442, 324/444, 446, 691, 693; 701/29, 30
See application file for complete search history.

(56) References Cited

U.S. PATENT DOCUMENTS

| | | | |
|---|---|---|---|
| 3,707,147 A * | 12/1972 | Sellers ........................ 600/525 |
| 5,049,738 A * | 9/1991 | Gergely et al. ............. 250/301 |
| 5,361,628 A | 11/1994 | Marko et al. |
| 5,660,181 A | 8/1997 | Ho et al. |
| 5,710,713 A * | 1/1998 | Wright et al. ................. 702/23 |
| 5,985,120 A | 11/1999 | Cholli et al. |
| 6,278,281 B1 | 8/2001 | Bauer et al. |
| 6,377,052 B1 | 4/2002 | McGinnis et al. |
| 6,380,746 B1 * | 4/2002 | Polczynski et al. ......... 324/446 |
| 6,433,560 B1 | 8/2002 | Hansen et al. |
| 6,549,861 B1 | 4/2003 | Mark et al. |
| 6,560,352 B1 | 5/2003 | Rowe et al. |

(Continued)

FOREIGN PATENT DOCUMENTS

EP    1 014 082    6/2000

(Continued)

OTHER PUBLICATIONS

Jianxun Hu, M.S., "The Characterization of Lubricating Fluids Using AC Impedance Spectroscopy", a dissertation, Dec. 2000, Milwaukee, WI.

(Continued)

*Primary Examiner*—Marc S. Hoff
*Assistant Examiner*—Manuel L. Barbee
(74) *Attorney, Agent, or Firm*—Rader, Fishman & Grauer PLLC

(57) ABSTRACT

Impedance spectroscopy is used to determine values associated with properties of a substance such as a fluid. In some embodiments, the present invention is applied to engine lubricants. A spectral matrix is constructed that comprises data taken from spectral plots. Also constructed is a result matrix comprising known quantities of a plurality of fluid constituents. A known analytic technique is performed on the spectral matrix to identify at least one principal component having significant influence on the spectral matrix. A reduced spectral matrix, wherein each column in the reduced spectral matrix is associated with a principal component having significant influence on the spectral matrix, is next created. A statistical technique uses the reduced spectral matrix and the result matrix to create at least one prediction equation. The prediction equation is used to predict at least one property in a second substance in situ.

100 Claims, 13 Drawing Sheets

U.S. PATENT DOCUMENTS

| | | | |
|---|---|---|---|
| 6,577,112 B1 * | 6/2003 | Lvovich et al. | 324/71.1 |
| 6,620,621 B1 | 9/2003 | Cohenford et al. | |
| 2003/0141882 A1 | 7/2003 | Zou et al. | |
| 2003/0208328 A1 * | 11/2003 | Pickerd | 702/67 |
| 2005/0104607 A1 * | 5/2005 | Byington et al. | 324/693 |

FOREIGN PATENT DOCUMENTS

| | | |
|---|---|---|
| EP | 1014082 A2 * | 6/2000 |
| EP | 1 111 383 | 6/2001 |
| FR | 2 820 824 | 8/2002 |
| GB | 2 288 022 | 10/1995 |
| WO | WO-03/019119 | 3/2003 |
| WO | WO-2004/077036 | 9/2004 |

OTHER PUBLICATIONS

"Principal Components Analysis" (downloaded on Nov. 25, 2003) from http://www.okstate.edu/artsci/botany/ordinate/PCA.htm.

Aapo Hyvarinen, "Principal Component Analysis", Apr. 23, 1999 (downloaded on Nov. 4, 2003) from http://www.cis.hut.fi/-aapo/papers/NCS99web/node5.html.

Jaakko Hollmen, "Principal Component Analysis", Mar. 8, 1996 (downloaded on Nov. 4, 2003) from http://www.cis.hut.fi/-jhollmen/dippa/node30.html.

"Principal Component Analysis" (downloaded on Nov. 4, 2003) from http://www.casaxps.cwc.net/FactorAnalysis.htm.

"Principal Components and Factor Analysis" (downloaded on Nov. 4, 2003) from http://www.statsoftinc.com/textbook/stfacan.html.

"Algorithms, The Beer Lambert Law" (downloaded on Nov. 26, 2003) from http://www.galactic.com/algorithms/beer_lambert.htm.

"Algorithms, Classical Least Squares (CLS)" (downloaded on Nov. 26, 2003) from http://www.galactic.com/algorithms/cls.htm.

"Algorithms, Discriminant Analysis, The Mahalanobis Distance" (downloaded on Nov. 25, 2003) from http://www.galactic.com/algorithms/discrim_mahaldist.htm.

"Algorithms, Discriminant Analysis, The PCA/MDR Method" (downloaded on Nov. 25, 2003) from http://www.galactic.com/algorithms/discrim_pca.htm.

"Algorithms, Inverse Least Squares" (downloaded on Nov. 25, 2003) from http://www.galactic.com/algorithms/its.htm.

"Algorithms, Least Squares Regression" (downloaded on Nov. 25, 2003) from http://www.galactic.com/algorithms/least_squares.htm.

"Algorithms, Partial Least Squares" (downloaded on Nov. 25, 2003) from http//www.galactic.com/algorithms/pls.htm.

"Algorithms, Principal Component Analysis Methods" (downloaded on Nov. 25, 2003) from http://www.galactic.com/algorithms/pca.htm.

"Algorithms, Principal Component Regression" (downloaded on Nov. 26, 2003) from http://www.galactic.com/algorithms/pcr.htm.

International Search Report dated Apr. 19, 2005 (3 pages).

Derwent English Abstract for EP 1 111 383 (1 page).

Delphion English Abstract for WO 02065086A2 (which is a family member of FR 2 820 824) (3 pages).

* cited by examiner

FIG. 9

| Results Matrix Sample | Hours | VIS100C | TBN | Fe | ZDDP950 | ZDDP655 | CO3_1512 | Oxid1719 | CO3_852 |
|---|---|---|---|---|---|---|---|---|---|
| 1_70 | 1 | 15.35 | 10.16 | 9 | -1.32E-03 | 2.26E-03 | 1.01E-03 | 5.74E-04 | -2.18E-04 |
| 102_70 | 102 | 15.72 | 8.84 | 21 | -1.98E-02 | -2.26E-02 | -7.15E-03 | 1.27E-04 | -2.34E-03 |
| 125_70 | 125 | 16.14 | 8.45 | 28 | -2.23E-02 | -2.54E-02 | -6.06E-03 | 1.32E-03 | -3.86E-03 |
| 149_70 | 149 | 16.54 | 8.1 | 34 | -2.38E-02 | -0.028522 | -4.90E-03 | 3.16E-03 | -3.51E-03 |
| 200_70 | 200 | 17.29 | 8.07 | 44 | -2.61E-02 | -3.61E-02 | -6.60E-03 | 4.90E-03 | -4.71E-03 |
| 225_70 | 225 | 17.76 | 7.96 | 51 | -2.74E-02 | -3.87E-02 | -7.16E-03 | 5.97E-03 | -4.78E-03 |
| 250_70 | 250 | 18.33 | 7.62 | 58 | -2.86E-02 | -4.27E-02 | -1.63E-02 | 6.60E-03 | -4.73E-03 |
| 275_70 | 275 | 18.79 | 7.19 | 60 | -0.029014 | -4.23E-02 | -1.67E-02 | 7.56E-03 | -5.41E-03 |
| 300_70 | 300 | 19.28 | 7.1 | 70 | -2.89E-02 | -4.18E-02 | -0.017433 | 9.22E-03 | -5.93E-03 |
| 325_70 | 325 | 19.93 | 6.6 | 71 | -2.97E-02 | -4.32E-02 | -1.89E-02 | 1.06E-02 | -6.40E-03 |
| 350_70 | 350 | 20.18 | 6.67 | 94 | -2.95E-02 | -4.36E-02 | -2.65E-02 | 1.28E-02 | -7.28E-03 |
| 378_70 | 378 | 21.43 | 5.83 | 93 | -3.07E-02 | -4.19E-02 | -2.60E-02 | 1.27E-02 | -6.25E-03 |
| 400_70 | 400 | 22.54 | 6.16 | 112 | -0.031374 | -4.19E-02 | -2.90E-02 | 1.57E-02 | -7.30E-03 |
| 50_70 | 50 | 15.41 | 9.48 | 14 | -1.14E-02 | -8.34E-03 | -3.54E-03 | -3.01E-04 | -1.37E-03 |
| 75_70 | 75 | 15.64 | 9.27 | 17 | -1.58E-02 | -1.60E-02 | -5.79E-03 | 2.23E-04 | -2.61E-03 |

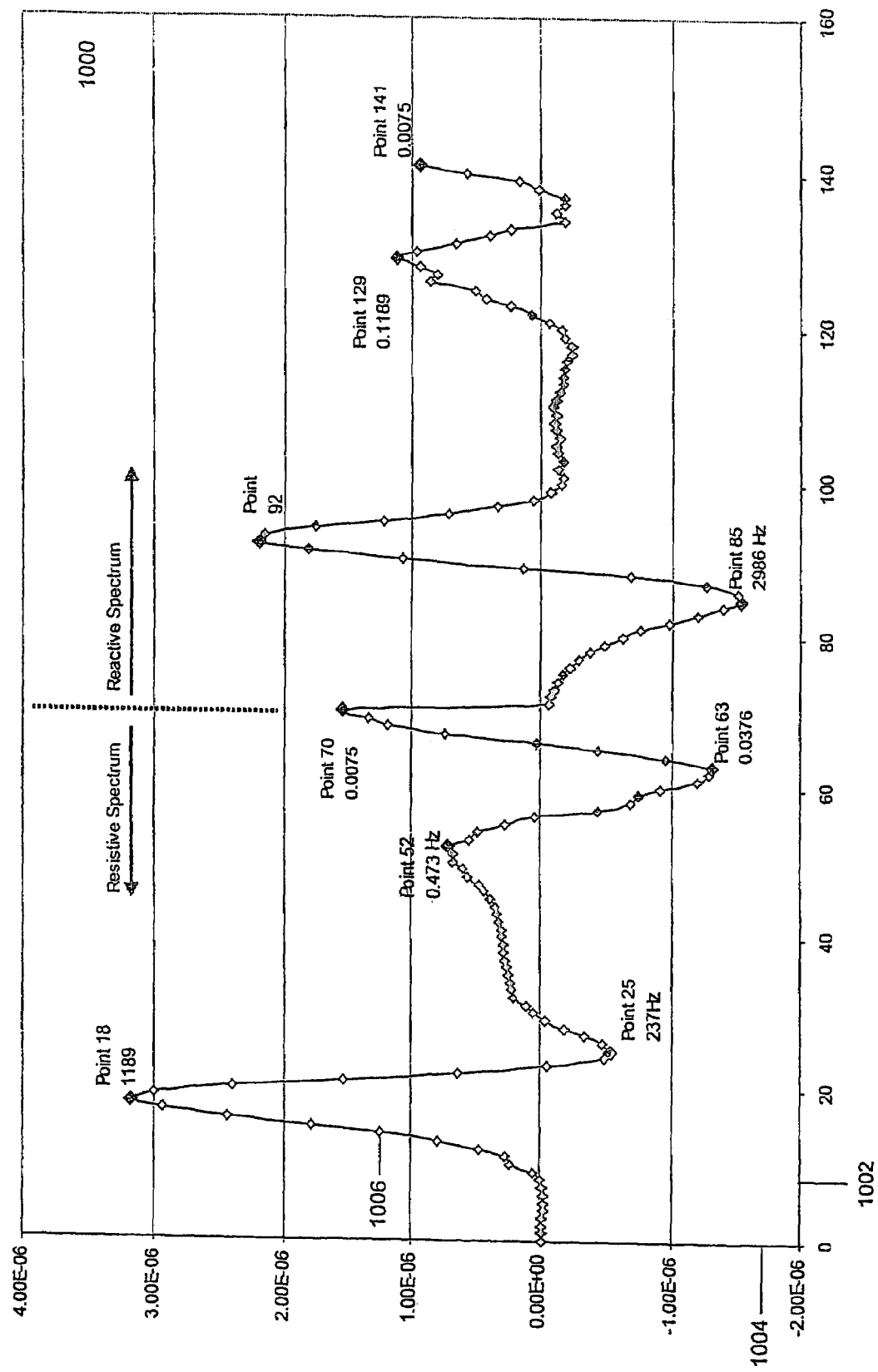

FIG. 11

| | 1104 | 1106 | 1108 | 1110 | 1112 | 1114 | 1116 | 1118 | 1120 |
|---|---|---|---|---|---|---|---|---|---|
| Reduced Matrix | | | | | | | | | |
| Freq | 1.19E+03 | 2.37E+02 | 4.73E-01 | 3.76E-02 | 7.50E-03 | 2.99E+03 | 5.96E+02 | 1.19E-01 | 7.50E-03 |
| log(Freq) | 3.0750613 | 2.375061219 | -0.324937 | -1.424928 | -2.124939 | 3.4750613 | 2.7750613 | -0.9249277 | -2.12493874 |
| Point | 18 | 26 | 52 | 63 | 70 | 85 | 92 | 129 | 141 |
| 1_70 | 5.69E+05 | 6.19E+05 | 7.14E+05 | 1.01E+06 | 1.41E+06 | -2.71E+05 | -8.67E+04 | -2.43E+05 | -5.75E+05 |
| 102_70 | 1.14E+06 | 2.88E+06 | 3.36E+06 | 4.29E+06 | 5.34E+06 | -8.51E+05 | -1.41E+06 | -6.94E+05 | -1.13E+06 |
| 125_70 | 1.11E+06 | 2.94E+06 | 3.44E+06 | 4.49E+06 | 5.61E+06 | -8.42E+05 | -1.47E+06 | -7.84E+05 | -1.21E+06 |
| 149_70 | 1.09E+06 | 3.00E+06 | 3.49E+06 | 4.72E+06 | 6.18E+06 | -8.39E+05 | -1.52E+06 | -9.92E+05 | -1.67E+06 |
| 200_70 | 1.08E+06 | 3.00E+06 | 3.49E+06 | 4.77E+06 | 6.85E+06 | -8.37E+05 | -1.52E+06 | -1.13E+06 | -2.31E+06 |
| 225_70 | 1.09E+06 | 2.93E+06 | 3.38E+06 | 4.61E+06 | 7.02E+06 | -8.35E+05 | -1.47E+06 | -1.21E+06 | -2.92E+06 |
| 250_70 | 1.08E+06 | 2.94E+06 | 3.37E+06 | 4.52E+06 | 7.24E+06 | -8.28E+05 | -1.48E+06 | -1.27E+06 | -3.68E+06 |
| 275_70 | 1.06E+06 | 2.87E+06 | 3.30E+06 | 4.36E+06 | 7.19E+06 | -8.12E+05 | -1.44E+06 | -1.20E+06 | -3.54E+06 |
| 300_70 | 1.06E+06 | 2.82E+06 | 3.22E+06 | 4.32E+06 | 6.95E+06 | -8.07E+05 | -1.41E+06 | -1.23E+06 | -3.72E+06 |
| 325_70 | 1.05E+06 | 2.72E+06 | 3.10E+06 | 4.16E+06 | 6.71E+06 | -7.89E+05 | -1.34E+06 | -1.16E+06 | -3.38E+06 |
| 350_70 | 1.05E+06 | 2.67E+06 | 3.04E+06 | 4.12E+06 | 6.36E+06 | -7.82E+05 | -1.30E+06 | -1.07E+06 | -2.62E+06 |
| 378_70 | 1.03E+06 | 2.63E+06 | 3.02E+06 | 4.09E+06 | 6.36E+06 | -7.67E+05 | -1.29E+06 | -1.07E+06 | -2.67E+06 |
| 400_70 | 1.01E+06 | 2.52E+06 | 2.89E+06 | 3.90E+06 | 6.07E+06 | -7.46E+05 | -1.22E+06 | -1.05E+06 | -3.05E+06 |
| 50_70 | 1.15E+06 | 1.96E+06 | 2.23E+06 | 2.84E+06 | 3.60E+06 | -7.53E+05 | -7.37E+05 | -4.59E+05 | -8.63E+05 |
| 75_70 | 1.16E+06 | 2.67E+06 | 3.08E+06 | 3.85E+06 | 4.61E+06 | -8.37E+05 | -1.24E+06 | -5.60E+05 | -9.03E+05 |

| Sample | Nyquist Z Min | Nyquist Z" Min | Freq @Z"Min | ZMax | Z Min | Bulk Circle to Z"min ||||| Interface Circle Z"min + 10 |||||
|---|---|---|---|---|---|---|---|---|---|---|---|---|---|---|
| | | | | | | Resistive Ct PT | Reactive Ct PT | Dep_Angle | Radius Bulk | Resistive Ct PT | Reactive Ct PT | Dep_Angle | Radius Interface |
| 1_70 | 2095900 | -37532 | 9.44194 | 3907800 | 4208.8 | 1047883 | 65108 | 3.56 | 1050118.72 | 3138420 | 199947 | 3.65 | 106481594 |
| 102_70 | 11658000 | -283590 | 2.37171 | 16498000 | 3294.4 | 5819789 | 290369 | 2.86 | 5834564.13 | 15764978 | 781997 | 2.84 | 4226105.28 |
| 125_70 | 11715000 | -281490 | 1.88391 | 16965000 | 3265.4 | 5849614 | 290440 | 2.84 | 5864160.38 | 17079312 | 867673 | 2.91 | 5471610.34 |
| 149_70 | 11738000 | -273980 | 2.37171 | 16954000 | 3258.8 | 5860227 | 292922 | 2.86 | 5875203.85 | 17514439 | 497181 | 1.63 | 5807015.18 |
| 200_70 | 12787000 | -319390 | 1.88391 | 17821000 | 3309.1 | 6142163 | 359224 | 3.22 | 6414970.33 | 21349284 | 653368 | 1.75 | 8593399.3 |
| 225_70 | 12306000 | -290760 | 1.88391 | 16639000 | 3306.7 | 6142163 | 344558 | 3.21 | 6159838.29 | 20587103 | 388856 | 1.08 | 8275157.53 |
| 250_70 | 12799000 | -307710 | 1.88391 | 16467000 | 3363.4 | 6395109 | 364032 | 3.26 | 6412324.74 | 20958648 | 100479 | 0.27 | 8131528.63 |
| 275_70 | 11761000 | -281450 | 2.37171 | 15407000 | 3371.2 | 5873212 | 369397 | 3.6 | 5893804.82 | 19880852 | 412517 | 1.19 | 8120311.69 |
| 300_70 | 11727000 | -282170 | 2.37171 | 15301000 | 3375.7 | 5862791 | 364941 | 3.56 | 5880778.9 | 19913203 | 393460 | 1.13 | 8186634.04 |
| 325_70 | 11662000 | -282020 | 1.88391 | 15198000 | 3376.4 | 5823038 | 402107 | 3.95 | 5846661.87 | 15579844 | -537200 | -1.97 | 3858274.04 |
| 350_70 | 11152000 | -262410 | 1.88391 | 14779000 | 3401.1 | 5575371 | 387312 | 3.97 | 5596058.75 | 18935533 | 319814 | 0.97 | 7775311.24 |
| 378_70 | 11197000 | -267330 | 1.88391 | 14852000 | 3364.7 | 5594586 | 439779 | 4.48 | 5622126 | 17881591 | 123201 | 0.39 | 6662867.11 |
| 400_70 | 11114000 | -274780 | 1.88391 | 14384000 | 3336.6 | 5548886 | 511812 | 5.27 | 5587754.89 | 18384635 | 197142 | 0.61 | 7251362.85 |
| 50_70 | 7157800 | -160790 | 3.7589 | 10660000 | 3468 | 3570901 | 199411 | 3.2 | 3583299.88 | 9884971 | 636159 | 3.68 | 2830721.4 |
| 75_70 | 10189000 | -225110 | 2.37171 | 14689000 | 3316.2 | 5083761 | 240722 | 2.71 | 5095882.1 | 13678585 | 555715 | 2.33 | 3564580.83 |

# FLUID CONDITION MONITORING USING BROAD SPECTRUM IMPEDANCE SPECTROSCOPY

BACKGROUND OF THE INVENTION

The present invention relates to monitoring the condition of a substance using impedance spectroscopy to indicate in real or near real time, i.e., while the substance is being used, the physio-chemical condition of a substance based on a correlation of measurements from electrical signals, using a statistical technique, to previously determined values.

The use of impedance spectroscopy techniques to monitor fluid conditions is previously known. For example, U.S. Pat. Nos. 6,433,560, 6,380,746, 6,377,052, and 6,278,281, along with U.S. Published Application 2003/0141882 of Zou et al., all assigned to the assignee of the present invention, all teach different configurations of electrodes for measuring current and then computing values for impedance. Further, the '281 patent teaches comparing the difference in currents at two frequencies with known bulk and interfacial impedance measurements to determine fluid conditions. Similarly, the '052 and '746 patents teach comparing the difference in impedance values calculated from exciting electrodes at two frequencies to determine fluid conditions.

The value of using impedance spectroscopy to monitor fluid conditions lies in the fact that it is desirable to be able to determine when a fluid, for example, an engine lubricant, has degraded to the point where it has either exhausted or come close to exhausting its useful life. Similarly, it is desirable to know how many hours of useful life remain with respect to a fluid sample. For an application such as monitoring the condition of an engine lubricant, it is desirable to be able to monitor the fluid condition while the engine is operating, as opposed to performing tests in a laboratory.

Lubricating fluids comprise three basic components: (1) base stock, (2) additives, and (3) contaminants. These components are known to influence the bulk and interfacial properties of the lubricant. Lubricating fluids possess interfacial properties, such as wear protection and corrosion protection, which are present at the interface between the fluid and the metal it protects. Different portions of the impedance spectrum correspond to bulk and interfacial properties. Previous applications of impedance spectroscopy have measured bulk properties and interfacial properties separately, but the capability of measuring the two together has not been previously appreciated. Accordingly, it would be desirable if bulk and interfacial properties could be measured together in order to give a more complete picture of the engine lubricant.

Existing methods of monitoring fluid conditions using impedance spectroscopy fail to contemporaneously measure a plurality of fluid properties. Rather, prior art methods, including those disclosed by the above-mentioned patents and publication, calculate impedance in different ways in order to determine a value for one fluid property. It can be shown that up to 90% of available information is not utilized when single parameter measurement techniques are employed. Thus, there is a need for systems and methods capable of implementing a multiple parameter function or functions to make quantitative measures of a broad range of fluid condition metrics.

BRIEF SUMMARY OF THE INVENTION

The present invention uses impedance spectroscopy to determine the amounts of additives, contaminants, and other components that are present in a fluid. In some embodiments, the present invention is applied to engine lubricants.

The invention comprises using the impedance spectrum to monitor the condition of a fluid in real time by disposing an electrode mechanism in the fluid and exciting the electrode mechanism sequentially with a specified number of alternating voltages, wherein each of the alternating voltages is at a different frequency in a range of frequencies. The invention measures the current in the electrode mechanism at each of said frequencies in the range of frequencies. From the measurement of current at each of the frequencies, resistive and reactive impedance values at each of the frequencies are calculated and used to predict at least one property in the fluid in situ.

In one embodiment, the invention comprises a method of analyzing a substance, comprising the steps of: (1) generating first and second plots of spectra over a range of frequencies; (2) creating a third plot that comprises the first and second plots by sequentially assigning x-values to selected frequencies in the first plot and selected frequencies the second plot; and (3) repeating steps (1)–(2) at least once to generate a plurality of third plots. Next, the method comprises building a spectral matrix that comprises data taken from the plurality of third plots and a result matrix comprising known quantities of a plurality of components in the substance. A Principal Component Analysis is performed on the spectral matrix to identify at least one principal component having significant influence on the spectral matrix. A reduced spectral matrix having at least one column, wherein each column in the reduced spectral matrix is associated with a principal component having significant influence on the spectral matrix, is next created. Then, a statistical technique is performed that uses the reduced spectral matrix and the result matrix to create at least one prediction equation. The at least one prediction equation is then used to predict at least one property in a second substance in situ.

In some embodiments, at least one datum derived from a Nyquist plot is added to the spectral matrix. The at least one datum derived from a Nyquist plot may include at least one datum from the bulk region of the Nyquist plot and at least one datum from the interfacial region of the Nyquist plot.

BRIEF DESCRIPTION OF THE DRAWINGS

FIG. 9 provides an example of a result matrix populated with data from laboratory tests representing conditions of an engine lubricant.

FIG. 10 shows regression coefficients plotted on a graph.

FIG. 11 shows a reduced spectral matrix.

FIG. 12 shows a chart giving examples of data, derived from a Nyquist plot of resistive impedance versus reactive impedance, that can be added to a combined Bode plot.

DETAILED DESCRIPTION OF THE INVENTION

System Overview

Figure 1:
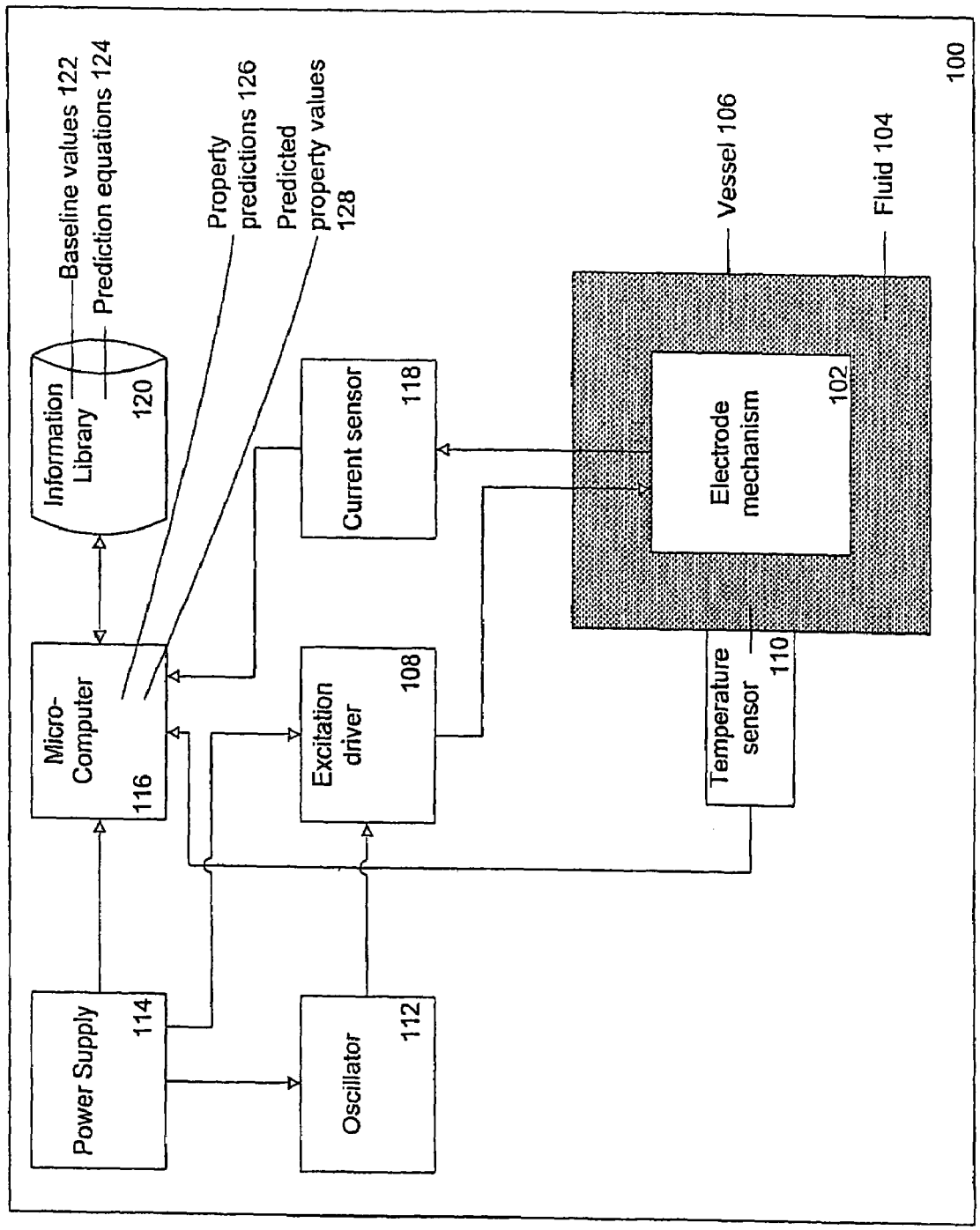
FIG. 1 depicts a system by which predictions of fluid conditions are made.

FIG. 1 provides an overview of an exemplary system 100 by which the condition of a substance such as a fluid is determined in real or near real time. Although the invention is described herein with reference to system 100, those skilled in the art will appreciate that other configurations and other components could support the claimed systems and methods so long as impedance spectroscopy is used to generate values for resistive and reactive impedance, which values could be used to perform calculations as described below to predict fluid conditions in situ and generally while the fluid is being actively used.

Electrode mechanism 102 is disposed in fluid 104 contained in vessel 106. The electrode mechanism may be any of those that are known in the art of impedance spectroscopy, including those described in aforementioned U.S. Pat. Nos. 6,433,560, 6,380,746, 6,377,052, and 6,278,281, and U.S. Published Application 2003/0141882 of Zou et al., all of which are hereby incorporated herein by reference. Present practice is to use the cylindrical probe mechanism disclosed in U.S. Published Application 2003/0141882 of Zou et al. In some embodiments of the present invention fluid 104 is an engine lubricant and vessel 106 is an engine crankcase.

Power supply 114 powers oscillator 112, a computing system or device such as microcomputer 116, and excitation driver 108. Excitation driver 108 receives an input from an oscillator 112. In one embodiment, oscillator 112 provides voltage in a range from approximately 75 kilohertz and 0.0075 hertz. However, those skilled in the art will appreciate that the invention could be practiced using voltages at frequencies higher than 75 kilohertz and/or lower than 0.0075 hertz. In one embodiment, oscillator 112 sequentially provides voltages at a specified number of different frequencies to excitation driver 108. Excitation driver 108, upon receiving input from oscillator 112, excites electrode mechanism 102, and current sensor 118 provides input to microcomputer 116. Present practice is for excitation driver 108 to provide voltages of approximately 250 millivolts RMS, although those skilled in the art will appreciate that the invention could be practiced using voltages at other levels. Temperature sensor 110 measures the temperature of fluid 104, and provides input to microcomputer 116.

Microcomputer 116 calculates and stores in memory values for resistive and reactive impedance, not shown in FIG. 1, based on the input from current sensor 118. Resistive and reactive impedance are sometimes referred to as real and imaginary impedance, respectively. Fluid temperature from temperature sensor 110 is input to computer 116. Baseline values 122, comprising previously predicted values of fluid properties, are stored in information library 120. Each of the baseline values 122 has as attributes the identity of the one fluid property with which it is associated, a fluid temperature, and a value representing the expended useful life of the fluid. Fluid temperature is usually expressed in degrees Celsius, and the value representing expended useful life may be expressed in hours. Baseline values 122 are determined in a laboratory external to system 100, and comprise expected fluid property values for a fluid of a given age at a given temperature. In some embodiments baseline values 122 comprise expected fluid property values for a fluid that has been used in an engine for a given number of hours, and is currently at a given temperature.

Microcomputer 116 uses information library 120 to determine the condition of fluid 104 by using the temperature input from temperature sensor 110 and the calculated values for resistive and reactive impedance to retrieve the correct prediction equations 124 from information library 120. Prediction equations 124 are described in detail below. Microcomputer 116 then uses prediction equations 124 to calculate fluid property values 128. Microcomputer 116 then obtains one or more property predictions 126 of values relating to the condition of fluid 104 by comparing at least one predicted fluid property value 128 to at least one of baseline values 122. Property predictions 126 will be stored in the memory of microcomputer 116, and may optionally be stored in information library 120, although this optional configuration is not depicted in FIG. 1.

In some embodiments, information library 120 is a component of microcomputer 116. In some embodiments, microcomputer 116 is further capable of providing as output an end of life (EOL) measurement, a remaining useful life (RUL) measurement, or both. In these embodiments, baseline values 122 are used in conjunction with the results from using the prediction equations 124, that is, fluid property values 128, to make a determination of whether fluid 104 is at or near the end of its useful life. Methods by which EOL and RUL determinations are made are discussed in more detail below.

Figure 2:
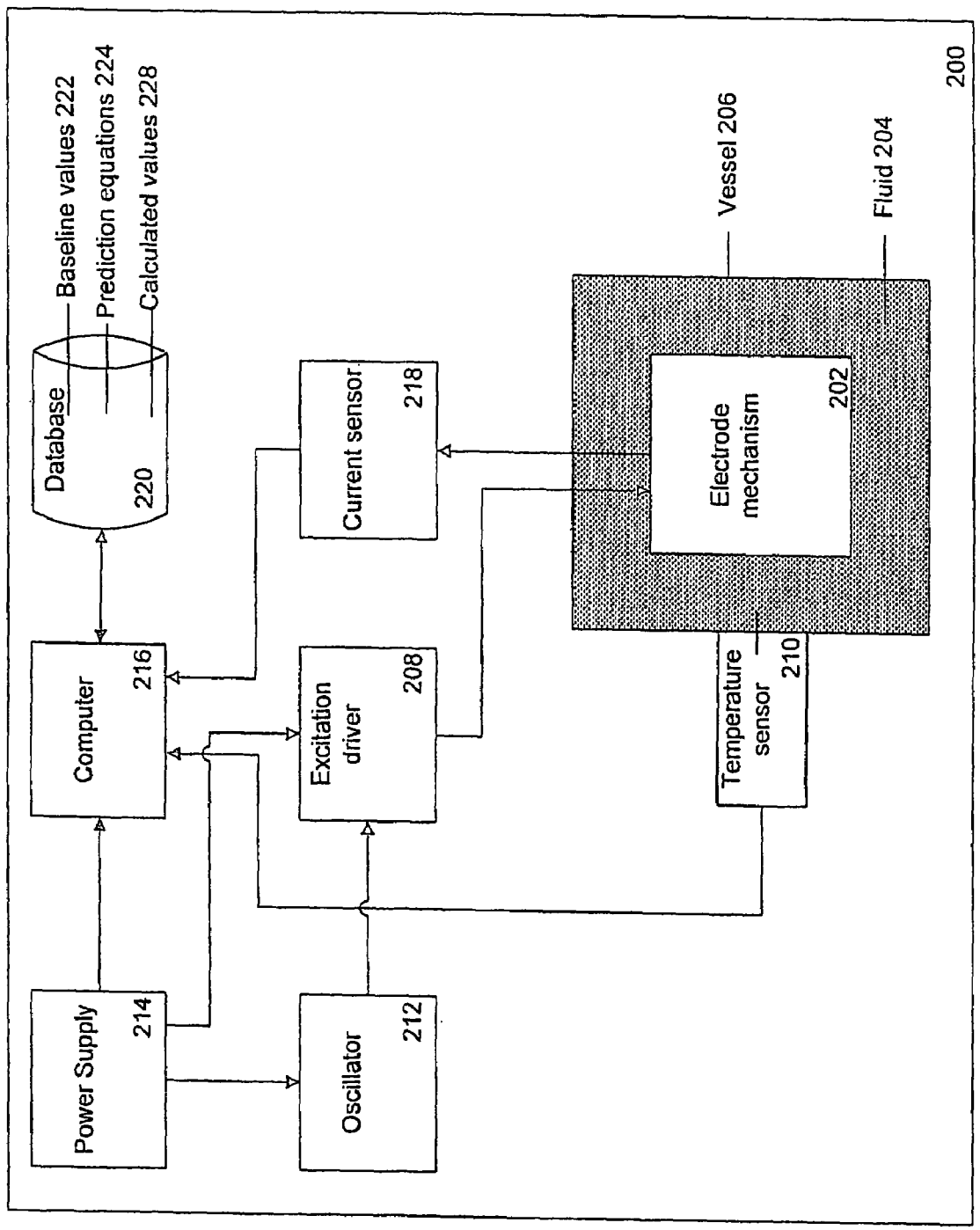
FIG. 2 describes a system that may be used for collecting data used to develop an information library used to predict fluid conditions.

FIG. 2 describes a system 200 that may be used for collecting data used to develop information library 120, including baseline values 122. Although the invention is described herein with reference to system 200, those skilled in the art will appreciate that other configurations and other components could support the claimed systems and methods so long as impedance spectroscopy is used to generate values for resistive and reactive impedance. System 200 includes a sample fluid 204 at a predetermined, constant temperature contained in a vessel 206. Electrode mechanism 202 is disposed in sample fluid 204. In one embodiment, sample fluid 204 is an engine lubricant.

Power supply 214 powers oscillator 212, a computing system such as computer 216, and excitation driver 208. Excitation driver 208 receives a sequence of inputs from oscillator 212. Oscillator 212 provides voltage at a specified number of frequencies in a range of frequencies. As currently practiced the invention uses frequencies in a range from approximately 75 kilohertz and 0.0075 hertz. However, those skilled in the art will appreciate that the invention could be practiced using voltages at frequencies higher than 75 kilohertz and/or lower than 0.0075 hertz. In one embodiment, the specified number of frequencies is 71. For each input from oscillator 212, excitation driver 208 excites electrode mechanism 202, and current sensor 218 provides input to computer 216. Present practice is for excitation driver 208 to provide voltages of approximately 250 millivolts RMS, although those skilled in the art will appreciate that the invention could be practiced using voltages at other levels. Temperature sensor 210 measures the temperature of fluid 204, and provides input to computer 216. Computer 216 generates calculated values 228 for resistive and reactive impedance based on the input from current sensor 218. Computer 216 stores the calculated values 228 in database 220 such that calculated values 228 are associated with the specified temperature and the frequency in the range of frequencies for which the calculated values for resistive and reactive impedance were obtained. In some embodiments, database 220 is a component of computer 216.

Computer 216 may be further configured to generate prediction equations 224 according to the method described in detail below. As part of this method, baseline values 222 are used to populate a result matrix, as described below. Prediction equations 224 may be stored in database 220. At some point prior to use of system 100 for prediction of fluid conditions in real time, prediction equations 224 may be copied from database 220 into information library 120 in system 100, wherein prediction equations 124 then comprise prediction equations 224. Similarly, baseline values 222 may be copied to baseline values 122.

Overview of a Method for Predicting Fluid Properties

Figure 3:
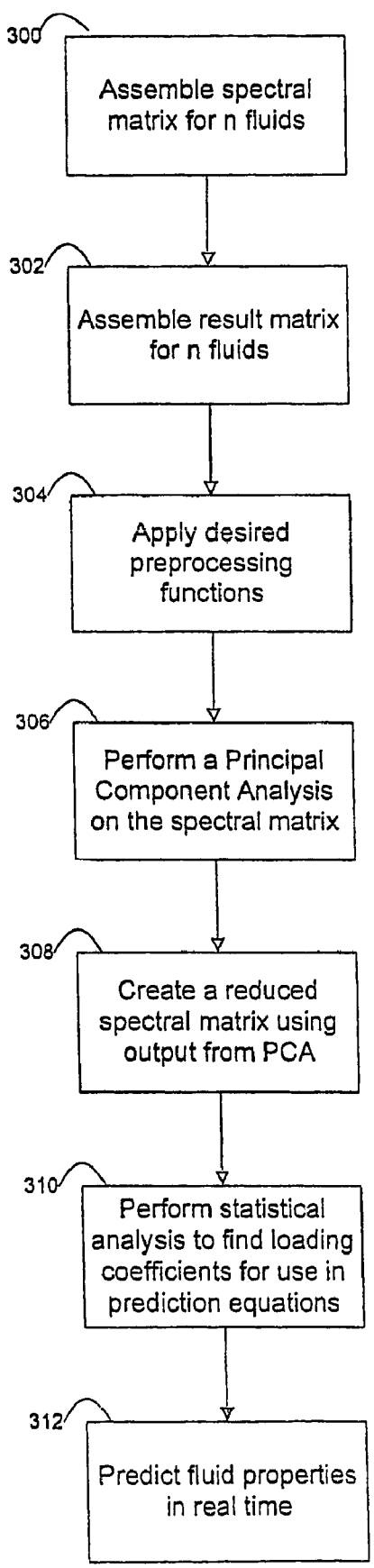
FIG. 3 depicts a flowchart providing an overview of the method by which an information library is developed and used to predict fluid conditions in real time.

FIG. 3 depicts a flowchart providing an overview of the method by which information library 120, including prediction equations 124 and baseline values 122, is developed and used to predict fluid conditions in real time. When reviewing FIG. 3 it is helpful to bear in mind that the overall goal of the process being described is to develop a set of prediction equations 124, each of which can be used to predict a fluid property. These prediction equations 124 will take the form:

$$Y_{ij}=b_0+b_1X_1+b_2X_2+\ldots+b_fX_f \quad (1)$$

where $Y_{i,j}$ represents the $j^{th}$ fluid property out of a given number of fluid properties being measured in the $i^{th}$ sample out of n fluid samples being used, each $X_1 \ldots X_f$ represents a value associated with an impedance reading at a particular frequency, and each $b_0 \ldots b_f$ is what is called a loading coefficient. One goal of the inventive method is to solve for the loading coefficients using values for $X_1 \ldots X_f$ determined from a process using impedance spectroscopy, certain statistical techniques, and baseline values 122 for $Y_{i,j}$ that are known from prior laboratory testing. The developed equations, i.e., prediction equations 124, can then be used to determine a set of values $Y_{i,j}$ in real time, i.e., the property predictions 126 described above with reference to FIG. 1.

Turning now to FIG. 3, block 300 represents the process of assembling a matrix of spectral data relating to a set of n fluids. In one embodiment, each of the n fluids will represent fluid conditions for the fluid at n different values for expended useful life. The goal of the process represented by block 300 is to develop a matrix of data, hereinafter referred to as the spectral matrix, representing impedance spectra obtained using each of the n fluids that can then be subjected to statistical analysis. The form of the spectral matrix is as follows:

$$\begin{vmatrix} X_{0,0}Y_{1,0} & X_{0,1}Y_{1,1} & \ldots & X_{0,p-1}Y_{0,p-1} \\ X_{1,0}Y_{1,0} & X_{1,1}Y_{1,1} & \ldots & X_{1,p-1}Y_{1,p-1} \\ \vdots & \vdots & \ddots & \vdots \\ X_{n-1,0}Y_{n-1,0} & X_{n-1,1}Y_{n-1,1} & \ldots & X_{n-1,p-1}Y_{n-1,p-1} \end{vmatrix}$$

The dimensions of the spectral matrix will be n rows by p columns, where n is the number of fluid samples, as discussed above, and p is related to, and sometimes equal to, the number of frequencies for which calculations of impedance have been used. In one embodiment p is equal to one-hundred and forty-two, and represents two times the number of frequencies for which impedance calculations have been used. The process of creating the spectral matrix is described in detail below with reference to FIG. 4.

Block 302 represents the process of assembling a result matrix for the n fluids, i.e., the same set of n fluids for which the spectral matrix was constructed in Block 300 above. As noted above baseline values 222 comprise data used in the result matrix. The data in the result matrix is achieved from traditional analytical laboratory procedures for measuring fluid properties. While by no means limited to the following, examples of the laboratory tests used to determine values for the result matrix include ASTM D-445 (40 or 100 degree vis), ASTM D-4739 (TBN), ASTM D-2869 (TBN, i.e., Total Base Number), ASTM D-664(TAN, i.e., Total Acid Number), ASTM D_5967 (per cent SOOT), and ASTM D-5185 (ICP Elementals). The form of the result matrix is as follows:

$$\begin{vmatrix} Y_{0,0} & Y_{0,1} & \ldots & Y_{0,f-1} \\ Y_{1,0} & Y_{1,1} & \ldots & Y_{1,f-1} \\ \vdots & \vdots & \ddots & \vdots \\ Y_{n-1,0} & Y_{n-1,1} & \ldots & Y_{n-1,f-1} \end{vmatrix}$$

The data in the result matrix represent fluid conditions with respect to f fluid properties in n sample fluids. Accordingly, the dimensions of the result matrix are n rows by f columns. The result matrix is used to find the loading coefficients for the prediction equations 124 (1), as discussed in more detail below. The process of creating the result matrix is described in further detail below with reference to FIG. 5.

Returning to FIG. 3, block 304 represents the optional process of applying pre-processing functions to the spectral matrix before subjecting the spectral matrix to statistical analysis. The pre-processing functions used in the present invention are all well known, and include but are not limited to mean-centering, taking the first or second derivative of the data, smoothing the data, sample averaging, and differencing. Differencing comprises taking the difference between two values related to a fluid sample, such as the difference between values for resistive and reactive impedance, or the difference between data values for a new fluid and a fluid that has been used, e.g., a new engine lubricant and a lubricant that has been used in an engine operating for a number of hours.

Block 306 represents the process of performing a Principal Component Analysis (PCA) on the spectral matrix. PCA is a technique for analyzing a set of data to determine underlying independent factors that influence the data. Applied in the context of the present invention, PCA provides the advantage of reducing the number of variables in the spectral matrix to a set of variables for which there are as few common variations in the data as possible. By using PCA to create a set of principal components that represent the major changes in the impedance spectra found in the spectral matrix, the present invention creates a simplified spectra that can be subjected to meaningful statistical analysis that would not be practical with the entire spectral matrix. The advantages of PCA can be seen by noting that in current practice of the present invention the number of columns in the spectral matrix is often reduced from one-hundred and forty-two to less than ten, allowing the creation of a set of meaningful data, wherein the size of the data set is such that it is practical to apply statistical techniques to the data. PCA in the context of the present invention is discussed in more detail below with reference to FIG. 6.

Block 308 represents the process of creating a reduced spectral matrix by redeveloping the spectral matrix with principal components selected from the output of the PCA. Specifically, as discussed below with reference to FIGS. 6 and 10, principal components are selected for the reduced spectral matrix if they show significant influence on the prediction of fluid properties. The selected principal components are then associated with the X values from the spectral matrix that correspond to them, and placed in the reduced spectral matrix. The process of creating a reduced spectral matrix is described in detail below with reference to FIG. 6.

Block 310 represents the process of performing a statistical analysis, using the result matrix and the reduced spectral matrix, to find loading coefficients that can be used in the prediction equations 124 (1) described above. Some embodiments of the present invention use Principal Component Regression (PCR) to determine the loading coefficients, while other embodiments use Multivariate Least Squares Regression (MLR) to determine the loading coefficients. PCR and MLR are both well known. Still other embodiments use well known nonlinear regression methods such as Group Methods of Data Handling. Additionally, other known methods of statistical analysis could be used to determine the loading coefficients. The use of statistical techniques in the context of the present invention is discussed in more detail below.

Block 312 represents the process of using the prediction equations 124 (1) in system 100 of FIG. 1 to obtain predicted property values 128. Predicted property values 128 are in turn compared with baseline values 122 to obtain property predictions 126. This processing may be done by microcomputer 116. In one embodiment, predicting fluid properties for a fluid in situ comprises determining the likely expended useful life of an engine lubricant by determining whether property predictions 126 either exceed or fail to meet predetermined threshold values, which determination may be done by microcomputer 116. From this determination an estimate of Remaining Useful Life (RUL) of the lubricant can be made and output using microcomputer 116. Similarly, if it is the case that, based on the determination of the likely age of the fluid, the fluid is near the end of its useful life, an End of Life (EOL) determination can be made and output from microcomputer 116. The procedure for making an RUL or EOL estimation in the context of the present invention is discussed in more detail below.

Creation of a Spectral Matrix

Figure 4:
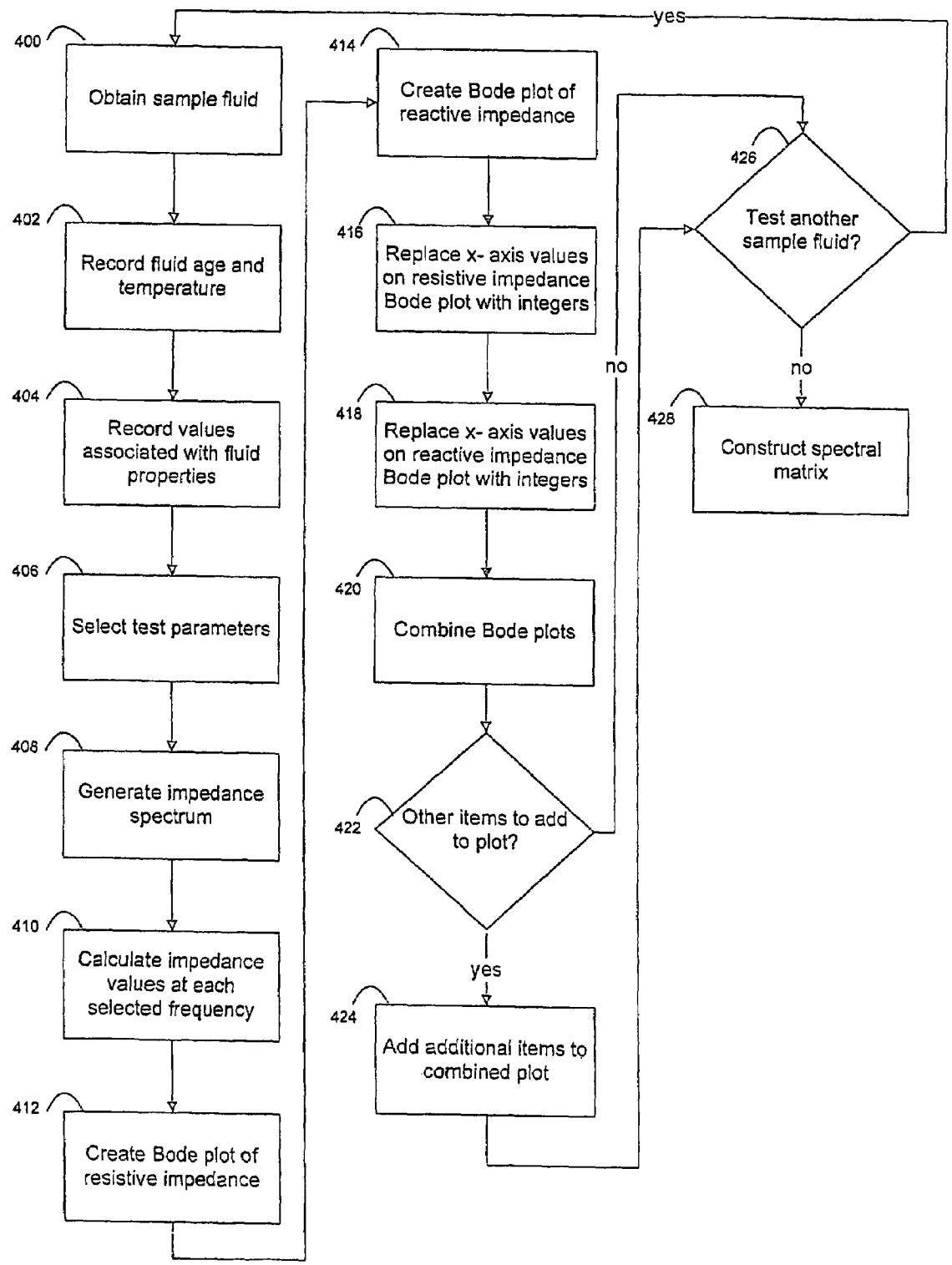
FIG. 4 provides a flowchart describing a method for building a matrix of spectral data, i.e., a spectral matrix.

FIG. 4 provides a flowchart describing an approach for building a matrix of spectral data. This approach is described herein with reference to system 200, although it is to be appreciated that other systems for conducting impedance spectroscopy, and recording and performing measurements and calculations therefrom, could be used. In step 400, a sample fluid 204 having a known expended useful life is provided at a specified temperature. In step 402, the expended useful life in hours and the specified temperature are recorded in database 220. It will be appreciated that recording the specified temperature is important inasmuch as many fluid measurements are a function at least in part of temperature. Similarly, many fluid measurements are a function at least in part of expended useful life. One of the objects of the present invention is to be able to determine a value for the expended useful life of a fluid when temperature is known.

In step 404, with reference to system 200, calculated values for resistive and reactive impedance 224 associated with predetermined properties of sample fluid 204 are recorded in database 220. Baseline values 222 are recorded in database 220 such that they are associated with the specified temperature of sample fluid 204 as well as the known age in hours of sample fluid 204. The predetermined fluid properties associated with baseline values 222 may include bulk and/or interfacial properties of the sample fluid 204 comprising amounts of additives such as zinc dithiodialkylphosphates (ZDDPs) and contaminants such as soot as well as interfacial properties such as wear protection. Baseline values 222 will have been previously determined through one of a variety of testing means known to those skilled in the art, as discussed above.

In step 406, test parameters are selected, comprising a range of frequencies to be tested, a specified number of specific frequencies in the range of frequencies to be tested, and the specific frequencies that will be tested. Present practice is to select 71 frequencies in the range from 75 kilohertz to 0.0075 hertz. A listing, in hertz, of frequencies used in at least one instance of present practice of the invention is as follows: 75000, 59574.62, 47321.8, 37589.04, 29858.04, 23717.08, 18839.15, 14964.47, 11886.7, 9441.941, 7500, 5957.462, 4732.18, 3758.904, 2985.804, 2371.708, 1883.915, 1496.447, 1188.67, 944.1941, 750, 595.7462, 473.218, 375.8904, 298.5804, 237.1708, 188.3915, 149.6447, 118.867, 94.41941, 75, 59.57462, 47.3218, 37.58904, 29.85804, 23.71708, 18.83915, 14.96447, 11.88670, 9.44194, 7.50000, 5.95746, 4.73218, 3.75890, 2.98580, 2.37171, 1.88391, 1.49645, 1.18867, 0.94419, 0.75000, 0.59575, 0.47322, 0.37589, 0.29858, 0.23717, 0.18839, 0.14964, 0.11887, 0.09442, 0.07500, 0.05957, 0.04732, 0.03759, 0.02986, 0.02372, 0.01884, 0.01496, 0.01189, 0.00944, and 0.0075. It should be understood that the invention is not limited to any particular frequencies, number of frequencies, or range of frequencies, and that the above list of frequencies is given for illustrative purposes only. The above-listed frequencies were chosen because they are somewhat evenly distributed across the impedance spectrum and have been found to yield good laboratory results.

In step 408, again referring back to system 200, oscillator 220 inputs a sequence of voltages at each of the specific frequencies selected to excitation driver 208, which sends current at each of the specific frequencies to electrode mechanism 202. Current sensor 218 detects the amount of current at each of the specific frequencies from electrode mechanism 202, and sends an amount of current as an input to computer 216.

In step 410, computer 216 calculates resistive and reactive impedance values for each of the specific frequencies based on the current at each of the specific frequencies, and stores the calculated values 224 in database 220.

In step 412, a Bode plot of the resistive impedance spectra is created. Bode plots are well known in the art. A Bode plot comprises a two-dimensional graph in which the x axis is comprised of the logarithms of the frequencies against which impedance is plotted, and the y axis is comprised of values for impedance. In step 414, a Bode plot of the reactive impedance spectra is created.

Figure 7:
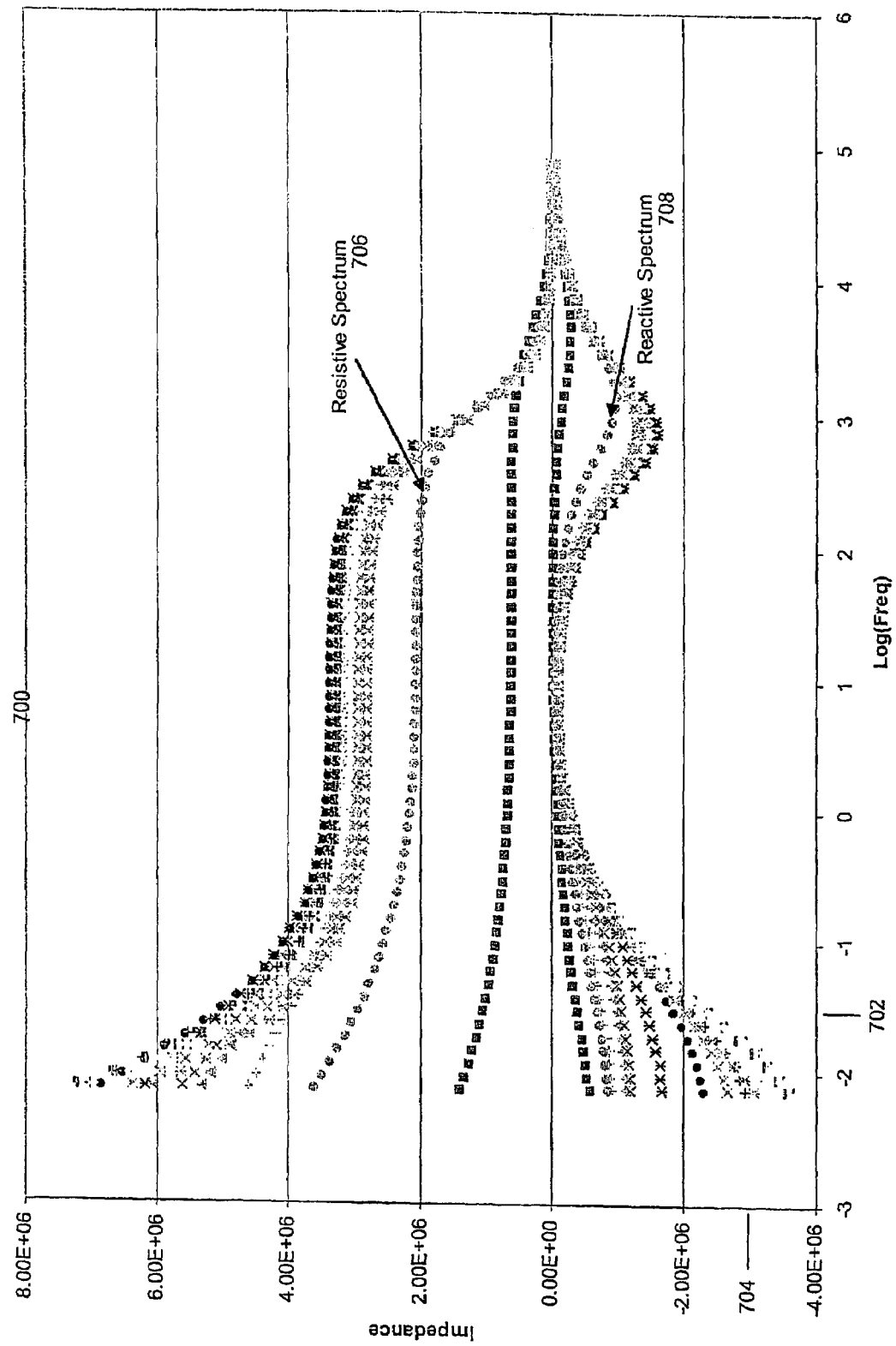
FIG. 7 shows Bode plots of resistive and reactive impedance spectra superimposed on the same graph.

FIG. 7 shows Bode plots of resistive and reactive impedance spectra superimposed on the same graph 700. X axis 702 comprises values for the logarithms of frequencies in the impedance spectra. Y axis 704 comprises calculated values for impedance corresponding to the frequencies whose logarithms are represented in x axis 702. Plots 706 comprise plots of the resistive impedance spectrum for different fluid samples. Plots 708 comprise plots of the reactive impedance spectrum for different fluid samples.

Returning to FIG. 4, in step 416 the values on the x axis of the Bode plot of the resistive impedance spectra are replaced with integers ranging from zero to a number one less than the specified number of frequencies that were selected in step 406. In step 418, the values on the x axis of the Bode plot of the reactive impedance spectra are replaced with integers ranging from the specified number of frequencies that were selected in step 406 to a number that is one less than two times the specified number of frequencies. For example, if the specified number of frequencies was seventy-one, values on the x-axis would range from zero to one-hundred and forty-one. As discussed below, the number of columns p in the spectral matrix is the number identified in the present step that is two times the specified number of frequencies. Present practice is to include one-hundred and forty-two columns in the spectral matrix.

In step 420, the Bode plot of the resistive impedance spectra created in step 412 and modified in step 416 is combined with the Bode plot of the reactive impedance spectra created in step 414 and modified in step 418. In one embodiment, the Bode plots of the resistive and reactive spectra are combined so that the plots are laid "head to tail", with the maximum plotted value on the x axis of the plot of the resistive impedance spectra one unit to the left of the minimum value on the x axis of the plot of the reactive impedance spectra. It should be understood that the order in which the Bode plots of resistive and reactive impedance are combined is not essential to the practice of the invention. For convenience, the approach and examples discussed herein place a Bode plot of resistive impedance to the left of a Bode plot of reactive impedance on a combined graph. This order could just as easily be reversed. In fact, points from the Bode plots of the resistive and reactive spectra could be placed on the combined plot in any order without making a difference to the results achieved by practicing the invention.

Figure 8:
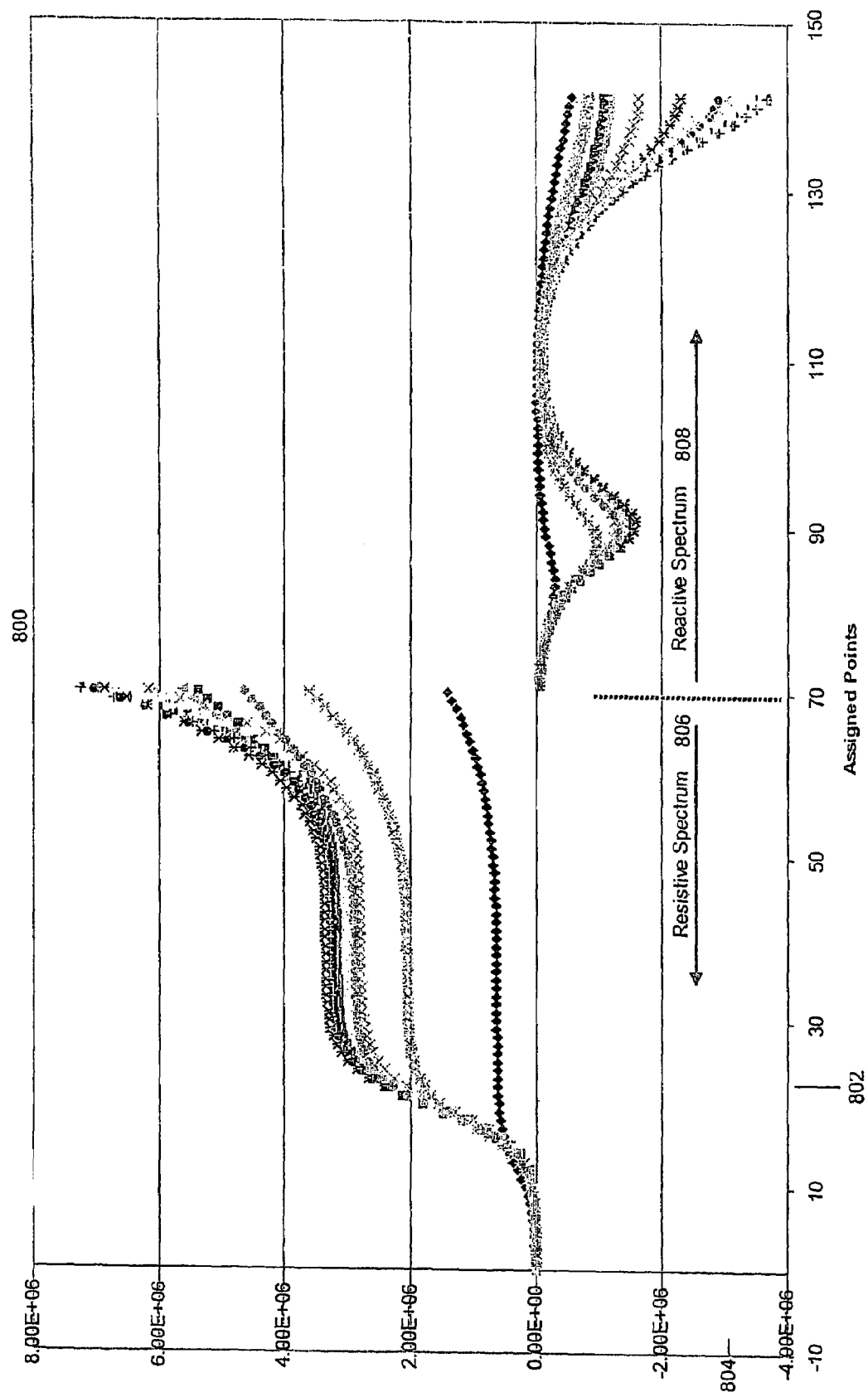
FIG. 8 shows an example of combined Bode plots on a graph.

FIG. 8 shows an example of combined Bode plots on a graph 800. Y axis 804, which comprises the same scale as found on y axis 704, comprises calculated values for impedance corresponding to the frequencies whose logarithms are represented in x axis 702. With respect to x axis 802, however, the logarithms of the frequencies in the impedance spectra have been replaced by integers ranging from zero to one-hundred and forty-one. Resistive impedance spectra 806 lie above the x axis values less than or equal to seventy. Reactive impedance spectra 808 lie above the x axis values greater than or equal to seventy-one.

Returning to FIG. 4, in step 422 a test is done to determine whether there are any other data points to be added to the combined plot. It has been found that adding certain data points to the combined plot can increase the ability of the invention to predict fluid properties. Examples of data points that may be added to the combined plot are discussed below with respect to FIGS. 12 and 13.

If there are other data points to be added to the combined plot, then they are added in step 424 by placing them either to the left of the minimum x value presently graphed on the combined plot, or to the right of the maximum x value currently graphed on the combined plot. If there are not any data points to be added to the combined plot, then the process continues to step 426.

In step 426, a test is done to determine if there is another sample fluid 204 to be tested. If the answer is yes, the method returns to step 400. If the answer is no, the method proceeds to step 428. In general, there will be n iterations of the method, n being the number of fluid samples at different ages that are being tested.

In step 428 a spectral matrix, taking the form described above, is constructed. As discussed above, the spectral matrix will have n rows and p columns. The number p generally represents the number of frequencies for which impedance readings are included in the matrix. However, as mentioned above, in one embodiment of the present invention, p is actually twice the number of frequencies for which impedance measurements were taken because resistive impedance and reactive impedance are placed together on combined plots. For example, in one embodiment impedance measurements are taken at seventy-one different frequencies, and p is therefore one-hundred and forty-two when resistive and reactive impedance plots are combined. Each number X, or x value, in the spectral matrix represents an integer from zero to p, and each number Y represents an impedance value on the combined graph associated with its corresponding x value.

Adding Data to the Combined Plot and Spectral Matrix

Figure 13:
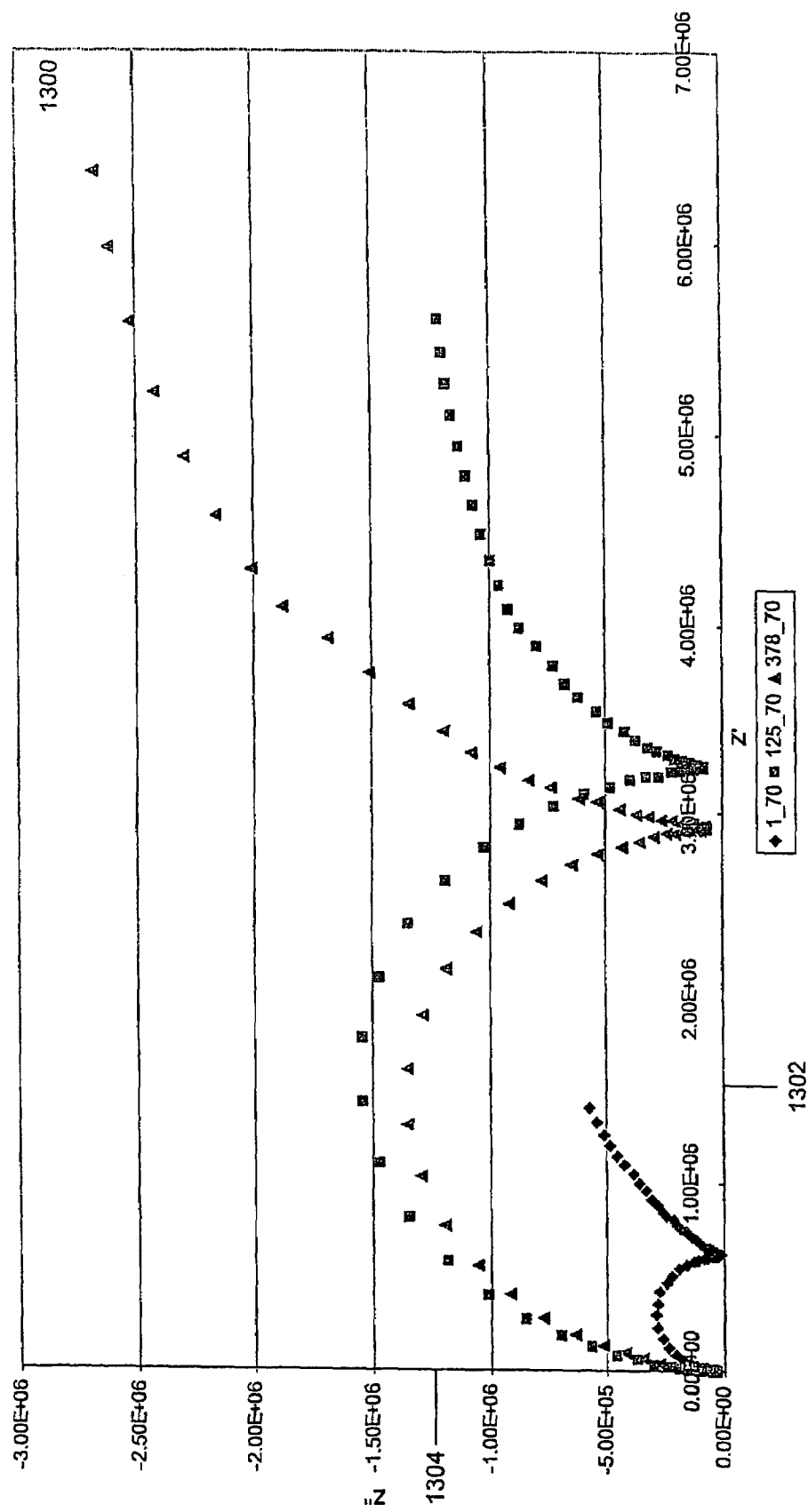
FIG. 13 shows a graph comprising three Nyquist plots for three different lubricating fluid samples.

FIG. 13 shows graph 1300 comprising three Nyquist plots of the impedance spectra for three different lubricating fluid samples. X-axis 1302 comprises values for resistive impedance, also known as real impedance, denoted Z'. Y-axis 1304 comprises values for reactive impedance, also known as imaginary impedance, denoted Z". As will be understood by those skilled in the art, for each of the three plots on graph 1300 the data points to the left of the minimum value for Z" represent the fluid bulk. Likewise, those skilled in the art will understand that the data points to the right of the minimum value for Z" for each of the three plots on graph 1300 represent the interfacial region between the fluid and metal. In one embodiment, the interfacial region would represent where the fluid is in contact with an engine. Some of the data points discussed below are not contained on the graph 1300 but will be known from data recorded from generating the impedance spectra.

FIG. 12 depicts chart 1200 giving examples of data that can be added to the combined plot derived from a Nyquist plot of resistive impedance versus reactive impedance. Column 1202 lists the identifiers for each of the samples for which data is provided. Note that the data in chart 1200 was taken from the same fluid samples as was used to generate the Bode plots shown in FIGS. 7 and 8. Further, although graph 1300 shows only three Nyquist plots, in actual practice of the invention a Nyquist plot would be generated for each of the data samples in column 1202.

Column 1204 represents the Z' value where Z" is minimum. Column 1206 represents the Z" value where Z" is minimum. As noted above, the point at which Z" is minimum denotes the boundary between the bulk and interface regions of the Nyquist spectrum.

Column 1208 represents the frequency in the spectra at which Z" is minimum. Graph 1300 does not represent this value. However, all of the values for Z" will be contained in the spectral matrix, and moreover, it is possible to determine from the spectral matrix the frequency in the impedance spectrum at which each value was recorded, inasmuch as the Bode plots used to create the spectral matrix originally contained the logarithm of frequency on the x axis.

Column 1210 represents the maximum Z' value within the total data set. In some cases this value is the "Nyquist Max," that is, the Z' value between the bulk and interfacial regions of the Nyquist spectrum. In other cases this value could be the Z' value for data points associated with the lowest or highest frequencies.

Column 1212 represents the minimum Z' value within the total data set. In some cases this value is the "Nyquist Min," that is, the Z' value between the bulk and interfacial regions of the Nyquist spectrum. In other cases this value could be the Z' value for data points associated with the lowest or highest frequencies.

Columns 1214, 1216, 1218, and 1220 all contain data associated with the points in the bulk region of the Nyquist spectrum, that is, the points between the origin of the graph and the minimum value for Z". As is known, these points describe a semicircle. Certain information about the semicircle, or the circle that would result from completing the semicircle, can be helpful in predicting fluid properties.

Column 1214 represents the Z' value for the centerpoint of the circle in the bulk region of the Nyquist spectrum, that is, the circle completed by the semicircle drawn from the leftmost point on the x axis on which data is plotted to the point on the x axis at which Z" is plotted. This circle is sometimes referred to as the bulk circle.

Column 1216 represents the Z" value for the centerpoint of the centerpoint of the bulk circle.

Column 1218 represents a measurement in radians of the angle between the x axis and a line drawn through the origin of the graph and the centerpoint of the bulk circle. This measurement is referred to as the depression angle of the bulk circle.

Column 1220 represents a calculation of the radius of the bulk circle.

Columns 1222, 1224, 1226, and 1228 all contain data associated with the points in the interfacial region of the Nyquist spectrum, that is by the points to the right on the x axis of the minimum value for Z". As is known, these points describe a semicircle. Certain information about the semicircle, or the circle that would result from completing the semicircle, can be helpful in predicting fluid properties.

Column 1222 represents the Z' value for the centerpoint of the circle in the interfacial region of the Nyquist spectrum, that is, the circle completed by the semicircle drawn from the points to the right on the x axis of the minimum value for Z". This circle is sometimes referred to as the interface circle.

Column 1224 represents the Z" value for the centerpoint of the interface circle.

Column 1226 represents a measurement in radians of the angle between the x axis and a line drawn through the origin of the graph and the centerpoint of the interface circle. This measurement is referred to as the depression angle of the interface circle.

Column 1228 represents a calculation of the radius of the interface circle.

The data in FIG. 12 can be added to the spectral matrix and used to predict fluid properties either by itself or alongside other values, such as the selected values for resistive and reactive impedance already discussed. This data can be included in the spectral matrix by placing it on a graph either to the left or to the right of the combined Bode plots discussed above. Some, only one, or all of the data points discussed above may be used. In addition, skilled artisans will recognize that adding other data related to a scan of the impedance spectrum is within the scope and spirit of the present invention.

Creation of the Result Matrix

Figure 5:
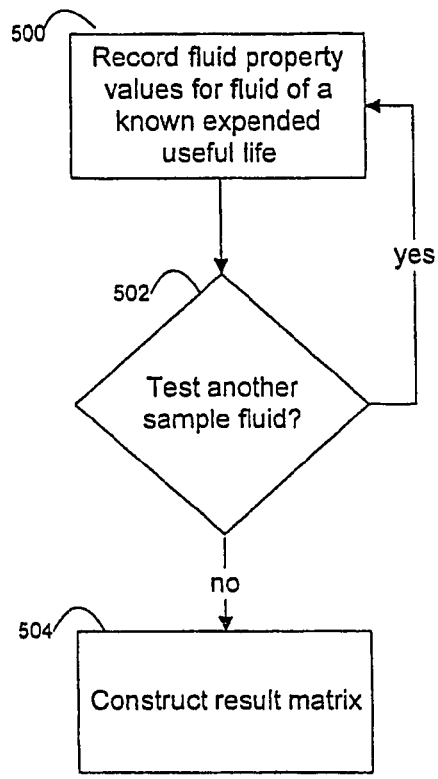
FIG. 5 provides a flowchart describing a method for building a result matrix.

FIG. 5 provides a flowchart describing a method for building a result matrix. In step 500, a fluid sample having a known expended useful life is tested in a laboratory to determine values for a predetermined set of fluid conditions, and these values are recorded. As discussed above with respect to FIG. 2, these values may be recorded in database 220 as baseline values 222. Some of the laboratory tests used in present practice are mentioned above with reference to block 302 in FIG. 3. In step 502, a check is done to determine whether there are more fluid samples to be tested. If the answer is yes, the process returns to step 500. If the answer is no, the method proceeds to step 504. In general, there will be n iterations of the method, n being the number of fluid samples having different expended useful lives that are being tested.

In step 504 a result matrix, taking the form described above with reference to block 302 of FIG. 3, is constructed. Each number $Y_{i,j}$ in the result matrix represents a fluid condition with respect to the jth fluid property from a total of f fluid properties tested in the ith fluid sample from a total of n fluid samples.

FIG. 9 provides an example of a result matrix 900 populated with empirically achieved data representing properties of an engine lubricant. Sample column 902 contains an identifier for each of the fluids represented in the result matrix. Hours column 904 contains the number of hours during which the lubricating fluid has been in operation in the engine, i.e., the expended useful life of the lubricating fluid. It should be understood that all of the data in the results matrix represents fluid conditions at a single temperature. Note that each value in column 904 contains the suffix "_70", which indicates that the data in result matrix 900 represents fluid conditions at seventy degrees Celsius.

Result columns 906, 908, 910, 912, 914, 916, and 918 each contain values representing the measurement of a particular fluid property determined by performing laboratory tests as described above. Result matrix 900 depicts fifteen sample lubricants in which seven fluid properties have been measured. Accordingly, when put into the form given above, result matrix 900 is a fifteen by seven matrix; that is, with respect to result matrix 900, n is fifteen, because 15 sample fluids have been analyzed, and f is seven.

Principal Component Analysis

Figure 6:
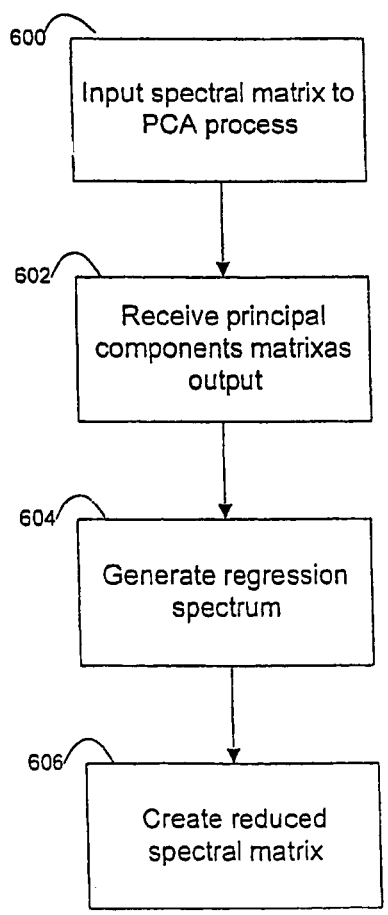
FIG. 6 shows the process by which the present invention uses Principal Component analysis (PCA).

FIG. 6 shows the process by which the present invention uses Principal Component analysis (PCA). PCA is a well known technique, described in a plethora of literature, including the articles "Principal Component Analysis Methods" and "Discriminant Analysis, The PCA/MDR Method", both incorporated by reference herein. Both of the foregoing documents were published to the world wide web by Thermo Galactic of Salem, N.H., and may be found by accessing its web site. PCA is also explained in the following, all of which are incorporated by reference herein: Michael Palmer, "Principal Component Analysis" published on the world wide web at the web site of the Department of Botany of the Oklahoma State University; StatsSoft, Inc., "Principal Components and Factor Analysis" published on the world wide web at the web site of StatSoft, Inc. of Tulsa, Okla.; "Principal Component Analysis"published on the world wide web at the web site of CasaXPS. Because PCA is well known, it will be described herein only to the extent necessary to explain how PCA is applied in the context of the present invention.

The goal of PCA is to reduce the number of elements in a data set by selecting principal components that are associated with the most variation in the data set. PCA comprises iteratively removing independent variations from a data set. Thus, in the context of the present invention the goal of PCA is to create a reduced spectral matrix that comprises a subset of the spectral matrix discussed above with respect to FIG.

4. PCA operating on spectral data uses the following relationship:

$$A = SF + E_A \quad (2)$$

where A is the n by p spectral matrix, S is an n by f score matrix, F is the f by p matrix containing the principal components, i.e., a principal components matrix, and $E_A$ is an n by p error matrix. F is sometimes referred to as a matrix of eigenvectors because it is used to recreate the spectral matrix. As above, n is the number of spectral samples in the spectral matrix and p is the number of data points represented in the spectra. The number f here represents the number of principal components. Thus, PCA applied to spectral data depends on the theory that the expression SF can be used to recreate spectral matrix A.

The actual calculations required for PCA in the present invention are performed by a statistical software package. Software packages that have been used to practice the invention include The Unscrambler® from Camo Technologies of Woodbridge, N.J.; Spectrum Quant+™ from PerkinElmer, Inc. of Wellesley, Mass.; and MatLab® from Mathworks, Inc. of Natick, Mass. Those skilled in the art will appreciate and understand the usage of such packages. Accordingly, the process described in FIG. 6 is relatively simple. At step, 600, the spectral matrix is provided as an input to the PCA process. At step 602, the aforementioned statistical software package provides output of the PCA process in the form of a principal component matrix.

At step 604, a set of regression coefficients associated with the principal components matrix is generated. This step serves the purpose of enabling selection of the principal components that appear to have a significant influence on the spectral matrix once the principal components are identified in the principal component matrix. That is, it is necessary to determine which principal components will be useful in recreating the spectral matrix, i.e., which principal components have significant influence over variations in the data set.

There are different known methods of identifying principal components, and the particular method used to select principal components is not critical to practicing the invention. However, present practice is to select principal components by generating a set of regression coefficients and plotting the regression coefficients over the points in the impedance spectra; this plot is called a regression spectrum. Regression coefficients are simply the set of coefficients obtained by regressing values in the impedance spectra against values representing known fluid properties, i.e., selected values from the result matrix. One skilled in the art will appreciate that standard statistical software packages, such as those discussed above, and a variety of regression methodologies, could be used to generate the regression spectrum.

Step 604 can be made clear by way of example. One fluid property measured in engine lubricants is Total Base Number (TBN). A predicted value for TBN with respect to a fluid sample at a given temperature and age can be retrieved from the result matrix, discussed above with reference to FIGS. 5 and 9, and regressed against the original impedance spectra generated as part of the process discussed above with reference to FIG. 4. Performing this regression generates a set of regression coefficients for TBN. These regression coefficients can then be plotted as shown in plot 1006 on graph 1000 of FIG. 10. X axis 1002 comprises integers in the range of the integers contained on the x axis of the combined Bode plot discussed above with reference to FIGS. 4 and 8.

Consistent with one embodiment referenced in examples previously given, plot 1006 is plotted from points zero to one-hundred and forty-one in relation to x axis 1002. Y axis 1004 comprises a range of values of coefficients generated from the regression of TBN against the impedance spectra.

A visual inspection of plot 1006 reveals that positive or negative peaks occur at points 18, 25, 52, 63, 70, 85, 92, 129, and 141 lying above x axis 1002. That is, the regression coefficients at these points have a significant magnitude, and these regression coefficients thus exert a relatively higher degree of influence over the prediction of a value for TBN than other regression coefficients in plot 1006. Accordingly, columns corresponding to points 18, 25, 52, 63, 70, 85, 92, 129, and 141 are selected from the spectral matrix and placed in the reduced spectral matrix in step 606.

It should be noted that, with respect to the above example, the present invention does not require using the regression spectrum for TBN, as opposed to other potentially available regression spectra, to pick points to be included in the spectral matrix. Other fluid properties, either individually as was the case with TBN in the above example, or in combination with one another, could have been used for this purpose. In this case, the regression spectrum for TBN was used because that regression spectrum was determined to lead to relatively accurate predictions of fluid properties. Other regression spectra may yield better results for other data sets.

FIG. 11 shows reduced spectral matrix 1100. Header row 1122 lists the points in the combined spectrum that have been identified as principal components. Column 1102 lists the identifiers for the fifteen different lubricants for which combined impedance spectra were generated. Note that the fifteen lubricants identified in column 1102 are the same fifteen samples identified in column 902 of result matrix 900. Columns 1104, 1106, 1108, 1110, 1112, 1114, 1116, and 1118 each contain values from the combined plots of the resistive and reactive impedance spectra for each of the fifteen lubricants. The identifiers in column 1102 are the same as the identifiers in column 902 contained in result matrix 900 depicted in FIG. 9; FIGS. 9 and 11 are based on the same laboratory test of the invention, and thus represent a result matrix and reduced spectral matrix respectively based on the same lubricating fluid samples.

Statistical Analysis of the Reduced Spectral Matrix

As discussed above with respect to block 310 of FIG. 3, a number of different statistical techniques, some of which use linear relationships and some of which use nonlinear relationships, may be used to identify coefficients for use in prediction equations (2) above. Linear regression methods with which the present invention may be practiced include but are not necessarily limited to Multivariate Least Squares Regression (MLR), also known as Multiple Linear Regression, Inverse Least Squares, or P-Matrix, as well as Principal Component Regression (PCR).

The present invention takes advantage of the following linear relationship:

$$R = PA + E \quad (3)$$

where result matrix R represents a concentration of a property or properties in a fluid, A represents a reduced spectral matrix, and coefficient matrix P is a matrix of loading coefficients. The matrix E is an error matrix, also known as the residual matrix, because it represents the difference between fluid properties estimated by the expression PA and the true value of fluid properties. It will be readily apparent to one skilled in the art that, where R and A are known, MLR can be performed to determine P. The matrix P in turn comprises coefficients that can be used in prediction equations 124 (1) to obtain predictions of property values, such as predicted property values 128, described above with reference to system 100.

PCR extends MLR to regress against the scores obtained from PCA as opposed to spectral data itself. Recall that the theory of PCA scores matrix S is that S can be used to reconstruct the spectral matrix A. Assuming that there is a linear relationship between spectral matrix A and concentration C, represented in the present invention by result matrix R, it is true that $$R=BS+E \qquad (4)$$

It will be readily apparent to one skilled in the art that, where R and S are known, MLR can be performed to determine B. The matrix B in turn comprises coefficients that can be used in prediction equations (2) to obtain predicted property values 128.

Nonlinear regression techniques with which the invention has been practiced include pattern recognition analyses, cluster analyses, and neural network analyses. One nonlinear regression technique that has been successfully applied in the present invention is the Group Method of Data Handling (GMDH) algorithm using the software program KnowledgeMiner available on the World Wide Web from Script Software. First, a software program such as Mathematica® from Wolfram Research, Inc. of Champaign, Ill., is used to read selected resistive and reactive impedance values for a given set of frequencies from a set of files. For example, approximately one frequency at each decade of the frequency range could be used. In one instance of practicing the invention impedance values at 10 kHz, 1 kHz, 100 Hz, 1 Hz, 0.1 Hz, 0.01 Hz were selected.

The next step is to calculate internal variables that assist in describing a geometric shape profile of each impedance spectra. These may consist of the length vector between each possible pair of two frequencies that have been collected. The angle, delta, of each selected point on the Nyquist representation of the spectra can be included; this angle is generally referred to as the dissipation factor, and the tangent of angle delta is calculated by dividing resistive impedance by reactive impedance. The tangent of angle delta represents the ratio of energy loss versus energy stored at a given frequency. Also, the inverse values of the afore-mentioned measured and internal variables are also calculated, allowing for variable combinations that include both quotients and products.

In order to determine the presence of redundancy in the variables a cluster analysis can be preformed. Cluster analysis is a statistical procedure that separates and groups a set of data into smaller sets of similar data. If multiple variables are found to be statistically similar, one variable from this variable cluster is selected. The resulting reduced variable set is then paired with an appropriate physio-chemical parameter to which a correlation is to be determined. This data is then modeled using Group Method for Data Handling, which is found in commercially available software, i.e., KnowledgeMiner. The resulting correlation could be considered a multi-layered neural network composed of connection weights that are polynomial, (including linear) functions.

Other applications of nonlinear regression techniques to the reduced spectral matrix may be apparent to skilled artisans. Further, skilled artisans will understand that the aforementioned linear regression techniques will be used to find loading coefficients for prediction equations 124 (1) that can in turn be used to obtain predicted property values 128.

RUL and EOL Determinations

As discussed above with respect to step 312 described in FIG. 3, predicted fluid properties can be used to estimate either the Remaining Useful Life (RUL) of the fluid, or when the fluid will reach its End of Life (EOL). Referring to FIG. 1, microcomputer 116 can be programmed with a variety of logical functions comparing baseline values 122 to the results of prediction equations 124 (1), namely property predictions 126, to determine a fluid's RUL and/or EOL.

As discussed above, each of the baseline values 122 has as attributes the fluid property for which the value was recorded, the age of the fluid sample with which the value is associated, and the temperature with which the value is associated. Measurements of RUL and EOL may take a variety of forms. For example, RUL may be expressed as a percentage of remaining useful life, as a percentage of useful life expended, as the number of miles a vehicle can be run before the fluid will reach EOL status, or as the number of hours for which an engine can be run before a fluid will reach EOL status. Similarly, EOL may represent a value for a fluid property at which the fluid has reached the end of its useful life or an age in hours at which the fluid has reached the end of its useful life.

In general, microcomputer 116 will be programmed with at least one logical function that evaluates an expression comparing one or more of the baseline values 122 with one or more of the property predictions 126. It should also be understood that the determination of RUL and EOL may be based on one or a plurality of fluid properties.

In the simplest case, determining RUL or EOL based on one fluid property, programming of microcomputer 116 could require iteratively evaluating the expressions ($Y>v_1$, $Y>v_2, \ldots, Y>v_n$) where Y is one of the property predictions 126, each value $v_i$ is one of the baseline values 122, and n is the number of fluid samples representing different fluid ages for which baseline values 122 have been stored in information library 120. Iterations would continue until one of the expressions ($Y>v_i$) evaluated to FALSE, i.e., until the program established that prediction of the fluid property value made in real time exceeded a threshold value, thus enabling the program to predict the age of the fluid based on the threshold value exceeded.

In a more general case, programming could iteratively evaluate a compound logical expression such as ($Y_1>v_{1,i}$ OR $Y_2>v_{2,i}$ OR ... OR $Y_{k>vk,n}$) where $Y_1 \ldots Y_k$ are property predictions 126, $v_{1,i} \ldots v_{k,n}$ are baseline values 122, k is the number of fluid properties being evaluated, and n is the number of fluid samples representing different fluid ages for which baseline values 124 have been stored in information library 120. Thus, if any of the fluid properties of interest fail to meet a threshold established by the relevant baseline values 122, the expression will evaluate to FALSE, and an RUL determination can be made based on the age attribute associated with $v_{1,i} \ldots v_{k,n}$. Similarly, microcomputer 116 could be programmed to make an EOL determination when any given threshold for EOL and/or RUL failed to be met. Also, the logical operator OR could be replaced by the logical operator AND in the logical expression, requiring that certain thresholds be met for all or at least a subset of property predictions 126 before and EOL and/or RUL determination is made.

The preceding discussion of the programming of microcomputer 116 is meant to be illustrative rather than limiting, inasmuch as a skilled artisan would recognize that a number of different algorithms could be implemented to make EOL and RUL determinations. Any determination of EOL and RUL using property predictions 126 or predicted property values 128 would be within the scope of the present invention.

Although not shown on FIG. 1, microcomputer 116 provides output of both RUL and EOL determinations. In one embodiment, for example, output of EOL determinations is manifested in the activation of a warning light on a vehicle console. In another embodiment, an RUL determination is manifested on a digital display embedded in a vehicle console. These examples are meant to be illustrative rather than limiting, inasmuch as any mode of outputting and displaying EOL and RUL determinations would be consistent with the present invention.

Alternative Embodiments

Figure 14:
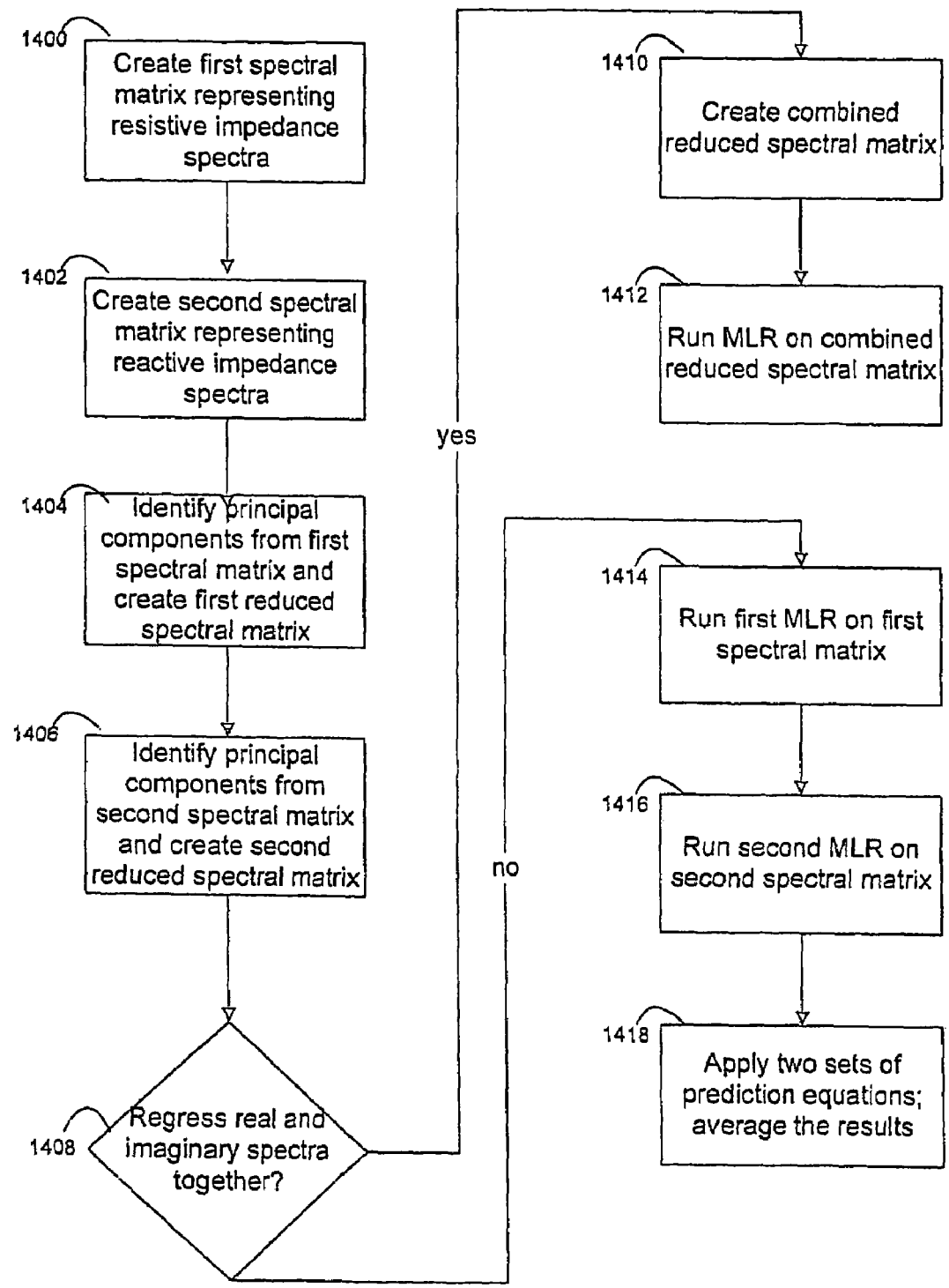
FIG. 14 describes an alternative embodiment in which data from each of the Bode plots of resistive and reactive impedance spectra are processed separately, with results then combined for use in predicting fluid properties.

The preceding disclosures of the invention assume that the spectral matrix is created as described in FIG. 4. According to the embodiment described in FIG. 4, Bode plots of resistive and reactive impedance spectra for a plurality of fluid samples are laid "head to tail" on a combined plot, and the data from the combined plot is then placed into the spectral matrix. FIG. 14 describes an alternative embodiment in which data from each of the Bode plots of resistive and reactive impedance spectra are processed separately, with results then combined for use in predicting fluid properties.

Prior to step 1400, steps 400 through 418 will have been performed as described above with reference to FIG. 4. However, instead of combining Bode plots as described with reference to step 420 and then creating a reduced spectral matrix as described with reference to step 428, in step 1400 a first spectral matrix is created solely from the resistive impedance spectra. Similarly, in step 1402, a second spectral matrix is created solely from the reactive impedance spectra.

Step 1404 follows the process discussed above with reference to FIG. 6 to perform PCA with respect to the first spectral matrix to create a first reduced spectral matrix. Similarly, step 1406 performs PCA with respect to the second spectral matrix to create a second reduced spectral matrix.

After step 1406 is complete, the invention can be practiced either by combining the first and second reduced spectral matrices and performing a regression on the resultant combined reduced spectral matrix, or by performing regressions on each of the first and second reduced spectral matrices and combining the results. Accordingly at step 1408 a check is done to determine whether regression is to be performed on the first and second reduced spectral matrices together or separately.

If regression is to be performed on the first and second reduced spectral matrices together, they are combined in step 1410. The first and second reduced spectral matrices will each have n rows, n being the number of fluid samples being tested, but may have different numbers of columns because the number of principal components identified for each of the first and second reduced spectral matrices may or may not be the same. The first and second reduced spectral matrices are combined simply by placing the data in the two matrices side by side, so that the combined reduced spectral matrix has n rows, and has the number of columns that is the sum of the number of columns in each of the first and second reduced spectral matrices.

In step 1412, MLR is performed with respect to the combined reduced spectral matrix in the same manner as described above with respect to the reduced spectral matrix. Similarly, the scores from the PCAs performed on the first and second spectral matrices could have been combined and a PCR or other statistical technique performed on the combined scores in the manner described above.

If the response to the check done in step 1408 is that regression is to be performed on the first and second reduced spectral matrices separately, a first MLR is performed on the first spectral matrix in step 1414. In step 1416, a second MLR is performed on the second spectral matrix. In step 1418 the results of the first and second MLRs are then used in the prediction equations 124 (1) in the manner described above, and the results of the prediction equations are then combined to yield final predictions of fluid properties. The results of prediction equations might be combined in a number of ways; in one embodiment they are averaged. Again, PCR or other statistical techniques also could have been performed in this manner.

Embodiments of the invention discussed thus far comprise using at least one Bode plot to create a spectral matrix. However, some embodiments of the invention create a spectral matrix without using data from a Bode plot, i.e., make a spectral matrix containing only Nyquist-derived datum values that are processed using the techniques that have been described above with respect to Bode plots. As discussed above with reference to FIG. 12, there is a considerable amount of data incidental to practicing impedance spectroscopy that is not contained in or derived from a Bode plot. For example, as discussed above regarding FIG. 12, data from Nyquist plots of impedance spectra has also been found to be useful when added to a combined Bode plot of resistive and reactive impedance, and then used to create a spectral matrix. Some embodiments of the present invention forgo the use of data from Bode plots and construct the spectral matrix solely from data such as the data discussed with reference to FIG. 12. Processing otherwise proceeds as described above with reference to FIG. 4.

The above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the field of determining fluid conditions using impedance spectroscopy and that the disclosed systems and methods will be incorporated into such future embodiments. Accordingly, it will be understood that the invention is capable of modification and variation and is limited only by the following claims.

We claim:

1. A method, comprising:
   (1) disposing an electrode mechanism in a substance;
   (2) exciting said electrode mechanism sequentially with a specified number of alternating voltages, wherein each of the alternating voltages is at a different frequency in a range of frequencies;
   (3) performing at least one calculation to generate at least one datum associated with each of the frequencies in the range of frequencies;
   (4) creating a graph comprising x-values related to the specified number; and
   (5) creating a combined plot by placing a plurality of plots generated from a plurality of spectra on the graph using each at least one datum, wherein each x-value corresponds to at most one datum in the combined plot.

2. The method of claim 1, further comprising repeating steps (1)–(5) at least once, thereby placing a plurality of combined plots on the graph, wherein each x-value corresponds to at most one datum in each combined plot.

3. The method of claim 2, further comprising building a spectral matrix that comprises at least two samples taken from the plurality of plots.

4. The method of claim 3, further comprising:
performing a Principal Component Analysis with respect to the spectral matrix;
analyzing the results of the Principal Component Analysis to identify at least one principal component having significant influence on the spectral matrix; and
creating a reduced spectral matrix having at least one column, wherein each column in the reduced spectral matrix is associated with a principal component having significant influence on the spectral matrix.

5. The method of claim 4, further comprising using a regression plot to analyze the results of the Principal Component Analysis.

6. The method of claim 4, further comprising applying a pre-processing function to the spectral matrix before performing a Principle Component Analyis on the spectral matrix.

7. The method of claim 4, further comprising building a result matrix comprising known quantities of a plurality of components in the substance.

8. The method of claim 7, further comprising performing a statistical technique that uses the reduced spectral matrix together with the result matrix to create at least one prediction equation for predicting properties in a second substance.

9. The method of claim 8, further comprising using the at least one prediction equation to predict at least one property in the second substance.

10. The method of claim 9, further comprising predicting the at least one property in the second substance in situ.

11. The method of claim 8, wherein the statistical technique is selected from the group consisting of Multivariate Least Squares Regression, Principle Component Regression, and Group Methods of Data Handling.

12. The method of claim 10, further comprising providing an end of life (EOL) indication for the substance when the amount of at least one of the at least one properties in the second substance has reached a predetermined value.

13. The method of claim 10, further comprising providing a remaining useful life (RUL) indication for the substance by comparing at least one of the at least one properties in the second substance to at least one baseline value for the substance.

14. A system, comprising:
an electrode mechanism that is operational when disposed in a substance;
a mechanism for exciting the electrode mechanism sequentially with a specified number of alternating voltages;
a computing device for performing at least one calculation to generate at least one datum associated with each of a plurality of frequencies in a range of frequencies, wherein the computing device is capable of receiving input from the electrode mechanism; and
at least one prediction equation that is generated at least in part by using the at least one datum.

15. The system of claim 14, further comprising a current sensor, wherein the computing device is configured to receive input from the current sensor.

16. The system of claim 14, wherein the at least one datum includes at least one value for resistive impedance and at least one value for reactive impedance.

17. The system of claim 14, further comprising an information library.

18. The system of claim 17, wherein the computing device comprises the information library.

19. The system of claim 17, wherein the information library comprises the at least one prediction equation.

20. The system of claim 19, wherein the computing device further comprises at least one predicted property value generated using the at least one prediction equation.

21. The system of claim 20, wherein the information library further comprises at least one baseline value.

22. The system of claim 21, wherein the computing device further comprises at least one property prediction for a second substance that is generated using the at least one predicted property value and the at least one baseline value.

23. The system of claim 22, wherein the computing device is configured to output a remaining useful life (RUL) indication.

24. The system of claim 22, wherein the computing device is configured to output an end of life (EOL) indication.

25. The system of claim 14, wherein the at least one prediction equation comprises at least one coefficient generated by using a statistical technique that uses a result matrix together with at least one reduced spectral matrix.

26. The system of claim 25, wherein the at least one reduced spectral matrix comprises data from at least one Bode plot of resistive impedance and at least one Bode plot of reactive impedance.

27. The system of claim 25, wherein the at least one reduced spectral matrix comprises data from at least one Nyquist plot.

28. The system of claim 25, wherein the at least one reduced spectral matrix is a combined reduced spectral matrix.

29. The system of claim 14, wherein the at least one prediction equation comprises at least one coefficient generated by combining:
at least one first interim coefficient generated by using a statistical technique that uses a result matrix together with a first reduced spectral matrix; and
at least one second interim coefficient generated by using a statistical technique that uses a result matrix together with a second reduced spectral matrix.

30. A method, comprising:
disposing in a substance an electrode mechanism that is operational when disposed in the substance;
exciting the electrode mechanism sequentially wit a specified number of alternating voltages;
performing at least one calculation to generate at least one datum associated with each of a plurality of frequencies in a range of frequencies; and
generating at least one prediction equation at least in part by using the at least one datum.

31. The method of claim 30, wherein the at least one datum includes at least one value for resistive impedance and at least one value for reactive impedance.

32. The method of claim 30, further comprising creating an information library.

33. The method of claim 32, wherein the information library comprises the at least one prediction equation.

34. The method of claim 30, wherein the at least one prediction equation comprises at least one coefficient generated by using a statistical technique that uses a result matrix together with at least one reduced spectral matrix.

35. The method of claim 30, wherein the at least one prediction equation comprises at least one coefficient generated by combining:
at least one first interim coefficient generated by using a statistical technique tat uses a result matrix together with a first reduced spectral matrix; and
at least one second interim coefficient generated by using a statistical technique that uses a result matrix together with a second reduced spectral matrix.

36. The method of claim 35, wherein the at least one reduced spectral matrix comprises data from at least one Bode plot of resistive impedance and at least one Bode plot of reactive impedance.

37. The method of claim 35, wherein the at least one reduced spectral matrix comprises data from at least one Nyquist plot.

38. The method of claim 35, wherein the at least one reduced spectral matrix is a combined reduced spectral matrix.

39. The method of claim 30, further comprising generating at least one predicted property value using the at least one prediction equation.

40. The method of claim 39, wherein the information library further comprises at least one baseline value.

41. The method of claim 40, further comprising generating at least one property prediction for a second substance using the at least one predicted property value and the at least one baseline value.

42. The method of claim 41, further comprising generating a remaining useful life (RUL) indication.

43. The method of claim 41, further comprising generating an end of life (EOL) indication.

44. A system for developing an information library, comprising:
an electrode mechanism that is operational when disposed in a first substance;
a mechanism for exciting said electrode mechanism sequentially with a specified number of alternating voltages, wherein each of the alternating voltages is at a different frequency in a range of frequencies;
a computing device for performing at least one calculation to generate at least one datum associated with each of the frequencies in the range of frequencies; and
at least one prediction equation tat is generated at least in part by using the at least one datum.

45. The system of claim 44, wherein the at least one datum includes at least one value for resistive impedance and at least one value for reactive impedance.

46. The system of claim 44, wherein the computing device is configured to receive as input a measurement of the current in the electrode mechanism at each of the frequencies in the range of frequencies.

47. The system of claim 44, wherein the range of frequencies is between approximately 75 kilohertz and 0.0075 hertz.

48. The system of claim 44, further comprising the computing device configured to create a graph comprising (1) at least one x-value related to the specified number and (2) a combined plot, wherein the data used to create the combined plot comprises the at least one datum associated with each of the frequencies in said range of frequencies.

49. The system of claim 48, wherein the data used to create the combined plot further comprises:
at least one datum from a first spectra comprising the at least one datum associated wit each of the frequencies in said range of frequencies; and
at least one datum from a second spectra comprising the at least one datum associated with each of the frequencies in said range of frequencies;
wherein each of the at least one datum from the first spectra and the at least one datum from the second spectra are associated with one of the at least one x-values.

50. The system of claim 49, wherein the first spectra comprises determined values for resistive impedance and the second spectra comprises determined values for reactive impedance.

51. The system of claim 48, wherein the data used to create the combined plot further comprises at least one datum derived from a Nyquist plot and the at least one datum derived from a Nyquist plot is associated with the at least one x-value.

52. The system of claim 51, wherein the at least one datum derived from a Nyquist plot includes at least one datum from the bulk region of the Nyquist plot and at least one datum from the interfacial region of the Nyquist plot.

53. The system of claim 48, wherein the graph further comprises a plurality of combined plots.

54. The system of claim 53, further comprising a spectral matrix that comprises at least two samples taken from the plurality of combined plots.

55. The system of claim 54, further comprising the computing device configured to perform a Principal Component Analysis wit respect to the spectral matrix.

56. The system of claim 55, further comprising the computing device configured to use the results of the Principal Component Analysis to create a reduced spectral matrix with at least one column.

57. The system of claim 56, further comprising a regression plot that is used to analyze the results of the Principal Component Analysis.

58. The system of claim 56, further comprising a preprocessing function that is applied to the spectral matrix before performing a Principle Component Analysis on the spectral matrix.

59. The system of claim 56, further comprising a result matrix comprising known quantities of a plurality of components in the first substance.

60. The system of claim 59, further comprising the computing device configured to perform a statistical technique that uses the reduced spectral matrix together with the result matrix to create the at least one prediction equation.

61. The system of claim 60, further comprising configuring the computing device to use the at least one prediction equation to predict at least one property in a second substance.

62. The system of claim 60, wherein the statistical technique is selected from the group consisting of Multivariate Least Squares Regression, Principle Component Regression, and Group Methods of Data Handling.

63. The system of claim 53, wherein the plot of the determined values for resistive impedance and the plot of the determined values for reactive impedance are Bode plots.

64. A method, comprising:
(1) generating a plurality of first plots of spectra over a range of frequencies;
(2) generating a plurality of second plots of spectra over the range of frequencies;
(3) repeating steps (1)–(2) at least once to generate a plurality of first plots and a plurality of second plots; and (4) creating a first spectral matrix from the plurality of first plots and a second spectral matrix from the plurality of second plots.

65. The method of claim 64, wherein each of the first plots is a plot of resistive impedance spectra and each of the second plots is a plot of reactive impedance spectra.

66. The method of claim 64, further comprising performing a first Principal Component Analysis on the first spectral matrix and a second Principal Component Analysis on the second spectral matrix.

67. The method of claim 66, further comprising:
using the results of the first Principal Component Analysis to create a first reduced spectral matrix having at least one column; and
using the results of the second Principal Component Analysis to create a second reduced spectral matrix having at least one column.

68. The method of claim 67, further comprising using a regression plot to analyze the results of the first Principal Component Analysis.

69. The method of claim 67, further comprising using a regression plot to analyze the results of the second Principal Component Analysis.

70. The method of claim 67, further comprising applying a pre-processing function to the first spectral matrix before performing the first Principle Component Analysis on the first spectral matrix.

71. The method of claim 67, further comprising applying a pre-processing function to the second spectral matrix before performing the first Principle Component Analysis an the second spectral matrix.

72. The method of claim 67, further comprising building a result matrix comprising known quantifies of a plurality of components in a substance.

73. The method of claim 67, further comprising:
performing a statistical technique that uses the first reduced spectral matrix together with the result matrix to create at least one first prediction equation; and
performing the statistical technique using the second reduced spectral matrix together with the result matrix to create at least one second prediction equation.

74. The method of claim 73, further comprising:
using at least one first prediction equation to determine at least one first predicted value relating to at least one property in a substance;
using at least one second prediction equation to determine at least one second predicted value relating the to at least one property in the substance; and
combining the at least one first predicted value and at least one second predicted value to predict the least one property in the substance.

75. The method of claim 74, further comprising predicting the at least one property in the substance in situ.

76. The method of claim 75, further comprising providing an end of life (EOL) indication for the substance when a value of at least one of the at least one properties in the substance has reached a predetermined threshold.

77. The method of claim 75, further comprising providing a remaining useful life (RUL) indication for the substance by comparing at least one of the at least one properties in the substance to at least one baseline value.

78. The method of claim 73, wherein the statistical technique is selected from the group consisting of Multivariate Least Squares Regression, and Group Methods of Data Handling.

79. The method of claim 67, further comprising building a combined reduced spectral matrix by combining the first reduced spectral matrix and the second reduced spectral matrix.

80. The meted of claim 79, further comprising adding data derived from a Nyquist plot to the combined reduced spectral matrix.

81. The method of claim 80, wherein the data derived from a Nyquist plot includes at least one datum from the bulk region of the Nyquist plot and at least one datum from the interfacial region of the Nyquist plot.

82. The method of claim 79, further comprising performing a statistical technique that uses the combined reduced spectral matrix and the result matrix to create at least one prediction equation.

83. The method of claim 82, further comprising using the at least one prediction equation to predict at least one property in a substance.

84. The method of claim 83, further comprising predicting the at least one property in the substance in situ.

85. The method of claim 84, further comprising providing an end of life (EOL) indication for the substance when the amount of at least one of the at least one properties in the substance has reached a predetermined threshold.

86. The method of claim 84, further comprising providing a remaining useful life (RUL) indication for the substance by comparing at least one of the at least one properties in the substance to at least one baseline value.

87. The method of claim 82, wherein the statistical technique is selected from the group consisting of Multivariate Least Squares Regression, Principle Component Regression, and Group Methods of Data Handling.

88. A method, comprising:
(1) generating a plurality of Nyquist plots, wherein each Nyquist plot is associated with a sample of a substance;
(2) creating derived data by deriving at least one datum from each of the Nyquist plots; and
(3) populating a spectral matrix with the derived data.

89. The method of claim 88, wherein the derived data includes at least one datum from the bulk region of the Nyquist plot and at least one datum from the interfacial region of the Nyquist plot.

90. The method of claim 88, wherein the derived data includes at least one of: a resistive impedance value where reactive impedance is minimum, a reactive impedance value where reactive impedance is minimum, a frequency at which reactive impedance is minimum, a maximum resistive impedance value within the total data set, a minimum resistive impedance value within the total data set, a resistive impedance value for the centerpoint of the circle in the bulk region of the Nyquist spectrum, a reactive impedance value for the centerpoint of the centerpoint of the bulk circle, a measurement in radians of the angle between the x axis and a line drawn through the origin of the graph and the centerpoint of the bulk circle, a calculation of the radius of the bulk circle, a resistive impedance value for the centerpoint of the circle in the interfacial region of the Nyquist spectrum, a reactive impedance value for the centerpoint of the interface circle, a measurement in radians of the angle between the x axis and a line drawn though the origin of the graph and the centerpoint of the interface circle, and a calculation of the radius of the interface circle.

91. The method of claim 88, further comprising performing a Principal Component Analysis on the spectral matrix.

92. The method of claim 91, further comprising:
analyzing the results of the Principal Component Analysis to identify at least one principal component having significant influence on the spectral matrix; and
creating a reduced spectral matrix having at least one column, wherein each column in the reduced spectral matrix is associated with a principal component having significant influence on the spectral matrix.

93. The method of claim 92, further comprising applying a pre-processing function to the spectral matrix before performing a Principle Component Analysis on the spectral matrix.

94. The method of claim 92, further comprising building a result matrix comprising known quantities of a plurality of components in the substance.

95. The method of claim 94, further comprising performing a statistical technique that uses the reduced spectral matrix together with the result matrix to create at least one prediction equation.

96. The method of claim 95, further comprising using the at least one prediction equation to predict at least one property in a second substance.

97. The method of claim 96, further comprising predicting the at least one property in the second substance in situ.

98. The method of claim 97, further comprising providing an end of life (EOL) indication for the second substance when the amount of at least one of the at least one properties in the second substance lass reached a predetermined value.

99. The method of claim 97, further comprising providing a remaining useful life (RUL) indication for the second substance by comparing at least one of the at least one properties in the second substance to at least one baseline value for the substance.

100. The method of claim 95, wherein the statistical technique is selected from the group consisting of Multivariate Least Squares Regression, Principle Component Regression, and Group Methods of Data Handling.

* * * * *